United States Patent
Vlasimsky

(10) Patent No.: US 12,327,356 B2
(45) Date of Patent: Jun. 10, 2025

(54) METHODS OF ASSESSING LUNG DISEASE IN CHEST X-RAYS

(71) Applicant: IMIDEX, INC., Denver, CO (US)

(72) Inventor: Richard Vlasimsky, Denver, CO (US)

(73) Assignee: IMIDEX, INC., Denver, CO (US)

( * ) Notice: Subject to any disclaimer, the term of this patent is extended or adjusted under 35 U.S.C. 154(b) by 0 days.

(21) Appl. No.: 18/754,934

(22) Filed: Jun. 26, 2024

(65) Prior Publication Data

US 2024/0346654 A1    Oct. 17, 2024

Related U.S. Application Data

(63) Continuation of application No. 17/545,383, filed on Dec. 8, 2021, now Pat. No. 12,039,724.

(60) Provisional application No. 63/123,183, filed on Dec. 9, 2020.

(51) Int. Cl.
| | | |
|---|---|---|
| *G06T 7/00* | (2017.01) | |
| *A61B 6/00* | (2006.01) | |
| *A61B 6/50* | (2024.01) | |
| *G06N 3/045* | (2023.01) | |
| *G06T 3/40* | (2006.01) | |
| *G06T 7/11* | (2017.01) | |
| *G06V 10/764* | (2022.01) | |
| *G06V 10/82* | (2022.01) | |
| *G16H 30/40* | (2018.01) | |
| *G16H 50/20* | (2018.01) | |

(52) U.S. Cl.
CPC .............. *G06T 7/0012* (2013.01); *A61B 6/50* (2013.01); *A61B 6/5217* (2013.01); *G06N 3/045* (2023.01); *G06T 3/40* (2013.01); *G06T 7/11* (2017.01); *G06V 10/764* (2022.01); *G06V 10/82* (2022.01); *G16H 30/40* (2018.01); *G16H 50/20* (2018.01); *G06T 2207/10116* (2013.01); *G06T 2207/20076* (2013.01); *G06T 2207/20081* (2013.01); *G06T 2207/20084* (2013.01); *G06T 2207/30061* (2013.01); *G06T 2207/30096* (2013.01); *G06T 2207/30168* (2013.01); *G06V 2201/032* (2022.01)

(58) Field of Classification Search
None
See application file for complete search history.

(56) References Cited

U.S. PATENT DOCUMENTS

| | | | | |
|---|---|---|---|---|
| 2020/0372650 A1* | 11/2020 | Furukawa | ............ | G06V 10/267 |
| 2021/0265043 A1* | 8/2021 | Haghighi | ............... | G16H 50/20 |

* cited by examiner

*Primary Examiner* — Leon Flores
(74) *Attorney, Agent, or Firm* — Thomas C. Meyers; Sullivan & Worcester LLP

(57) ABSTRACT

The present system provides methods and systems of detecting lung abnormalities in chest x-ray images using at least two neural networks.

12 Claims, 22 Drawing Sheets

METHODS OF ASSESSING LUNG DISEASE IN CHEST X-RAYS

TECHNICAL FIELD

The present disclosure relates to methods and systems for assessing lung disease in images of the lungs of a subject.

BACKGROUND OF THE INVENTION

Chronic respiratory diseases, such as lung cancer, cause approximately 1 in 15 deaths in the United States. Between 1980 and 2015, the mortality rate due to chronic respiratory diseases increased almost 30%.

As of 2018, more than 2.1 million new cases of lung cancer had been identified worldwide. The American Cancer Society estimated that in 2020 in the U.S., 228,820 new cases of lung cancer will be diagnosed, and 135,720 people will die from lung cancer.[1] In the U.S., lung cancer is by far the leading cause of cancer death among both men and women, making up almost 25% (1.76 million) of all cancer deaths. Each year, more people die of lung cancer than of colon, breast, and prostate cancers combined.

One of the reasons why lung cancer is the leading cause of cancer deaths is due to challenges to early detection and diagnosis. Approximately 57% of lung cancer cases are diagnosed at the last stage, Stage IV, where the cancer has metastasize. The five-year survival rate for Stage IV ranges from 5% to 15%. Conversely, the five-year survival rate for early Stage I cases ranges from 59% to 92%. However, only 17% of cases are identified at an early enough stage to intervene with a high chance of survival. Early identification of lung cancer will lead to greater survivability.

Lung cancer is typically detected through radiographs, such as X-rays and chest computed tomography (CT) scans, when a nodule appears in the lung. Unfortunately, X-ray examinations can be highly unreliable for cancerous nodule detection, with over 50% of cancerous nodules overlooked during X-ray examination. Low-dose CT (LDCT) scans have also been used to screen people at higher risk on an annual basis.

Radiologists manually analyze X-ray and CT images and there is a high level of skill involved in identifying a small or isolated pulmonary nodule. Successful detection by manual analysis varies by the radiologist's skill level and expertise. The variation in the capacity for detection is evidenced by the fact that malpractice claims for lung cancer are the highest percentage of outpatient claims. In a study of 8265 radiologists, 32.4% had at least 1 malpractice suit, and failure to diagnose lung cancer made up 42.5% of diagnostic errors (78% of the total suits). A similar study found that nearly 50% of malpractice cases in primary care setting were the result of missed cancer diagnoses, with lung cancer being a significant percentage of those suits.

In addition, the clinical sensitivity of manual characterization of lung nodules for malignancy is 70% in clinical practice. That leads to one third of patients being put at risk of an invasive surgical resection, bronchoscopy, or biopsy that a pathological examination later deems unnecessary. As a result, these patients are exposed to complications from surgery or death, and the cost burden of lung cancer treatment to the healthcare system could have been avoided.

SUMMARY OF THE INVENTION

The invention provides systems and methods for analyzing chronic pulmonary diseases, such as lung cancer, using machine learning (ML) systems that detect lung nodules in chest x-rays. Preferred systems of the invention use at least two neural networks that analyze a chest x-ray. A first neural network analyzes the entire chest x-ray, preferably at a reduced resolution to improve throughput, and provide a "global" analysis of whether the x-ray contains lung nodules. A second neural network analyzes subsections of the x-ray, preferably using object detection or tiling or rastering, to provide "local" analyses of whether specific locations in the x-ray contain lung nodules. ML systems can be trained using training data that includes chest x-rays, CT scans, and known pathologies to correlate features in chest x-rays with lung nodules. In addition, CT scans can be used to "ground truth" the ML systems' analyses of chest x-rays (i.e., as a check of the ML system's accuracy). Training data may be obtained from distributed sources and ML subsystems at those sources can update the ML system with the training data, for example, by using federated learning, without removing any private or confidential information from a source. The ML systems of the invention are thus able to detect lung nodules in chest x-rays with novel and unprecedented accuracy, as shown by an area under curve of true positives over false positives of at least about 0.74.

According to the invention, ML systems are trained to correlate features in x-rays with data obtained from CT scanning. Those features may be imperceptible to a trained human technician. Nevertheless, the ML systems of the invention can correlate them to features in CT scans associated with a chronic lung pathology. In doing so, the ML systems leverage CT scanning data to improve the diagnostic utility of x-ray imaging. Using these ML systems, which include multiple neural networks, expands access to accurate and effective disease screening, which is especially beneficial for regions that lack sufficient CT scanning capabilities.

In certain aspects, the invention provides systems for detecting lung abnormalities. Systems of the disclosure may include an image pre-processing module that resizes a chest x-ray image to produce a first image at a down-sampled or up-sampled resolution and segments the image into at least one subsection of the image that represents an organ of a body and a collection of neural networks, trained using a plurality of network architectures. The collection of neural networks includes at least a first neural network that analyzes the first image and, and a second neural network that analyzes the subsection of the image, wherein the neural networks of the collection each independently make an inference as to the presence of an abnormality. The system includes an ensemble classifier that reports the presence of an abnormality at a location in the lung using the collection of neural network inferences as inputs. Each neural network of the collection may be, for example, one of Faster R-CNN, Inception-Resnet, DenseNet, or NasNet (e.g., preferably with no two being the same). In some embodiments, the system first analyzes the image for quality and positioning accuracy and is operable to reject an image from further processing and provide a real-time notification instructing a technician to acquire another image. For example, the system may apply one or more exclusion criteria to the image, which optionally include patient age, over exposure, under exposure, or content of image metadata. Optionally, the pre-processing module (i) checks for image quality and positioning, (ii) standardizes image brightness and contrast, and/or (iii) standardizes the image across a plurality of images acquisition devices.

In certain embodiments, the system includes a feature engineering module that creates features from the collections of neural networks and provides the features as inputs for the ensemble classifier. The ensemble classifier may use averaging, logistic regression, a generalized linear model, or a random forest algorithm.

In preferred embodiments, the subsection (for the "local" image analysis) is at an original first resolution of the chest x-ray image and the first image (for the "global" image analysis) is at a lower second resolution than the original resolution. The collection of neural networks may include a third neural network. In some embodiments, the system parses the image into one or more segments (e.g., as adjacent "tiles" or overlapping pieces from a raster) where each image segment may include an image of intermediate resolution. The third neural network may analyze the image segments at the intermediate resolution to make an inference as to the presence of an abnormality. In some embodiments, the system segments the image to select a subsection by performing an object detection operation on the image to create a region proposal for an object detected in the image, and then selects the subsection from within the region proposal. In some embodiments, the second neural network assigns a confidence score to the bounded potential objects. The second neural network may classify potential objects as detected objects using the likelihood score. The second neural network may classify objects by creating a heatmap of bounded potential objects and their corresponding confidence scores and classifies objects using the heatmap.

In certain aspects, the present invention also includes ML systems trained using data from various sources separated by time and/or geography. These training data can include, for example, chest x-ray images, CT scans, and pathology results. Distributed ML subsystems can be placed at, or connected to, those locations and can update the central ML system. In certain embodiments, distributed systems include computer hardware with machine learning systems stored therein, in which the hardware is shipped (e.g., by overland freight and/or by air) to the clinical sites (e.g., hospitals or research institutions) where the data are located. Additionally or alternatively, the distributed ML systems may be connected (e.g., transiently, e.g., for a few hours or days) to the data at those clinical sites. A federated learning model can be used to update the ML system using data analyzed by the subsystems. By using such an arrangement, the ML systems of the invention can be trained using data from distributed sources, while ensuring that confidential patient data do not leave a hospital or other research institution. Moreover, in certain aspects, the ML systems or subsystems can preprocess data to eliminate biases or artifacts attributable to different instruments, e.g., CT scanners from different manufacturers.

In certain aspects, the present invention provides a system for detecting lung abnormalities in a subject. The system may include an image pre-processing module. The module may (i) resize a chest x-ray file to produce a first image at a down-sampled resolution, and (ii) place a subsection of the of the chest x-ray file into a second image at an original resolution of the chest x-ray file. The system may further include a first and a second neural network. The first neural network analyzes the first image to output a first set of scores indicating probabilities of nodules at locations in the lung. The second neural network analyzes the second image to output a second set of scores of probabilities of a nodule at a location in the lung. The neural networks may have been trained using chest x-ray images, lung CT scans, lung PET-CT scans, and/or clinical outcome data. The system may also include an ensemble classifier that reports the presence of the nodule in the location in the lung using the first set of scores and the second set of scores as inputs.

In certain aspects, the system may further also include a feature engineering module that creates features from the first and second sets of scores and provides the features as inputs for the ensemble classifier. The ensemble classifier may be, for example, a machine learning model trained using chest x-ray images, lung CT scans, lung PET-CT scans, and/or clinical outcome data. In certain aspects, the ensemble classifier is a random forest.

In certain systems of the disclosure, the second neural network performs an object detection operation on the chest x-ray file, creates a bounding box for an object detected in the file, and selects the subsection for the second image from within the box. The detected objects may include sub-visual objects.

In certain systems, the second neural network detects objects in the second image by detecting potential objects in portions of the image and bounding the potential objects on the image. The second neural network may assign a confidence score to the bounded potential objects. In such systems, the second neural network may classify potential objects as detected objects using the confidence score. The second neural network may discard potential objects that do not meet a confidence score threshold. In certain systems, the second neural network classifies objects by creating a heatmap of bounded potential objects and their corresponding confidence scores and classifies objects using the heatmap. The second neural network may include, for example, a Fast R-CNN and/or a region proposal network.

The present disclosure also provides methods for training a machine learning system to detect indications of pathologies in chest x-rays. Such methods may include training a machine learning system to detect, in chest x-ray images from patients with known pathology results, features associated with the pathology results; providing CT scans from a subset of the patients to the machine learning system; and operating the machine learning system to compare detected features from the chest x-ray images to the CT scans to affirm or negate the detected features associated with the pathology results in the training step.

The machine learning system may be trained using training data that includes the chest x-ray images, the pathology results, and the CT scans. However, this data may only be available at a plurality of sources separated by time and/or geography. Thus, the methods for training may include connecting the machine learning system to the plurality of sources at different times or locations and sending the training data from the connected sources to the machine learning system. This can be accomplished, for example, by shipping one or more computer systems with a machine learning system architecture to different clinical sites and physically connecting the computer systems to data stores at the sites. The distributed computer systems may include ML subsystems. These ML subsystems can be used in a federated learning model to train the machine learning system. Advantageously, when using this distributed architecture, the subsystems can be directed to avoid sending any confidential patient data to the machine learning system and thereby comply with applicable privacy regulations.

Similarly, the training methods of the disclosure can include using training data sets that include diverse CT scans different instruments operating under diverse imaging conditions or parameters. Diverse CT scans may include scans from different sources separated by time and/or geography.

In such situations, the methods may include reconstructing a standardized CT scan from each of the diverse CT scans. In certain aspects, the standardized CT scans include one or more features associated with a particular CT imaging instrument. The standardized CT scans may be used by the machine learning system as the ground truth to affirm or negate the detected features associated with the pathology. In certain aspects, the standardized CT scans can be created by distributed ML subsystems. The distributed ML systems may include a generative adversarial network (GAN) that is used to create the standardized CT scans.

In certain aspects, the x-ray images and/or CT images are annotated by a human-in-loop. The x-ray images and/or CT images may be annotated, for example, with electronic medical record data and/or bioassay data.

In certain methods of training, prior to training the system using chest x-ray images, the system is trained using images that do not contain a lung.

The invention also provides certain methods that further include: providing a chest x-ray image from a subject to the machine learning system; and operating the machine learning system to detect lung nodules in the chest x-ray image from the subject.

The present invention also provides a diagnostic method that includes operating a machine learning system to detect lung nodules. An exemplary method includes providing an image file of a chest x-ray from a patient to a machine learning system. The system may operate by shrinking the image file of the chest x-ray into a first image that depicts the entire x-ray at a reduced resolution and copying a subsection of the file into a second image at an original resolution; analyzing the first and second images in parallel by respective first and second neural networks to output scores indicating a probability of a nodule, wherein the machine learning system has been trained to learn associations between features in chest x-rays and known pathology results with an area under the curve (AUC) of true positives over false positives for learned feature associations is at least 0.74; and operating the machine learning system to detect lung nodules. In certain aspects, the AUC is between 0.74 and 0.83. The AUC≥0.74 may be achieved by unsupervised learning without the aid of a human once learning is initiated.

In certain aspects, the diagnostic method may include a machine learning system that has been trained on training data only available at a various sources separated by time and/or geography and the training comprises connecting the machine learning system to the sources at different times and/or locations. Connecting the machine learning system to the various sources may provide a federated learning model by which confidential patient information does not leave any of the sources. The machine learning system may include a plurality of distributed machine learning (ML) subsystems using a federated learning model to provide the machine learning system trained to detect the indications of pathology in chest x-rays.

The machine learning system may be further trained on CT scans from the subjects to affirm or negate learned feature associations. In certain aspects, CT scans are obtained as diverse CT scans from different instruments operating under diverse imaging conditions or parameters. In such instances, the method may further include reconstructing a standardized CT scan from each of the diverse CT scans. The system may include a GAN trained to reconstruct standardized CT scans from the diverse CT scans.

In certain aspects, the method further includes a human-in-loop training step. This training step may include: displaying the chest x-ray to a clinician; receiving at the machine learning system an annotation from the clinician that identifies a lung nodule in the chest x-ray; comparing by the machine learning system the annotation to one of the scores indicating a probability of a nodule; and using the comparison to improve learned feature associations.

The method may also include the machine learning system providing an alert that the system detected a lung nodule in the chest x-ray. The method can further include triaging the chest x-ray for immediate review by a human.

In certain aspects, the method also includes characterizing an identified lung nodule with the machine learning system. Characterizing may include, for example, classifying a nodule as a tumor, benign and/or malignant, and/or assessing or predicting nodule progression, volumetric sizing, nodule etiology, nodule histology, and/or a treatment response. A classified tumor may by analyzed using the system using Response Evaluation Criteria in Solid Tumour guidelines.

DETAILED DESCRIPTION

The invention provides systems and methods for analyzing chronic pulmonary diseases, such as lung cancer, using a machine learning (ML) system with at least two neural networks that analyze a chest x-ray image. Employing multiple neural networks allows the systems and methods of the invention to detect lung abnormalities (e.g., lung nodules) in chest x-rays with unprecedented accuracy.

In certain methods and systems, one of the neural networks analyzes an entire chest x-ray image. Due to the large size of many chest x-ray images, the image's resolution may be reduced or down-sampled for this entire-image assessment. A second neural network analyzes one or more subsections of the x-ray image at the image's original resolution. The present inventors found that, surprisingly, using multiple neural networks reduces or eliminates issues with localization and object detection encountered when using a single neural network. This, in turn, allows the ML systems of the invention to detect lung abnormalities in x-rays with increased accuracy.

The systems and methods of the invention may employ ML systems trained using data sets that include lung CT scans and chest x-ray images. The systems can be trained to correlate features in the chest x-rays with those in the CT scans. These features may be imperceptible to a human technician analyzing a chest x-ray or CT scan, and yet may be associated with a particular disease or pathology by the systems. The features in x-ray images correlated with those in CT scans can serve to confirm and/or ground truth an assessment of the x-ray image. Thus, the methods and systems of the invention can leverage data obtained from CT scanning to improve the more commonly-available x-ray imaging.

In certain aspects, the present invention also includes ML systems trained using data from various sources separated by time and/or geography. The training data may include, for example, chest x-ray images, CT scans, and known pathology results from patients at distributed hospitals or other research settings. Distributed ML subsystems can be emplaced at these various locations and trained using local data. The trained ML subsystems can then update the central ML system, for example, using a federated learning model. By using such an arrangement, the ML systems of the invention can be trained using data from distributed sources, while ensuring that confidential patient data does not leave a hospital or other research institution. Moreover, in certain aspects, the ML systems or subsystems can preprocess data to eliminate biases or artifacts attributable to different instruments, e.g., CT scanners from different manufacturers.

Figure 1:
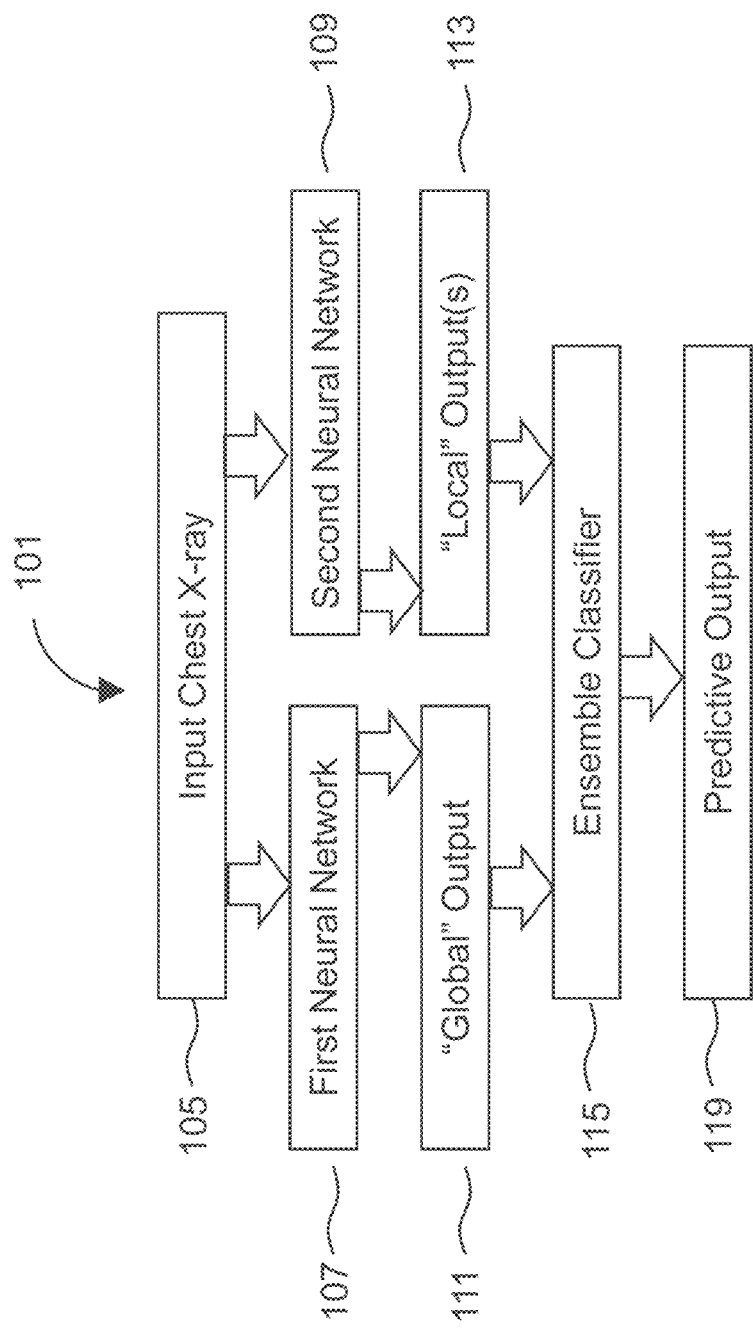
FIG. 1 shows an exemplary machine learning (ML) system of the invention.

FIG. 1 provides a general schematic of a machine learning system 101 of the present disclosure. A chest x-ray from a subject is used as an input 105 into the system 101 as a data file and/or image. The system 101 includes at least a first neural network 107 and a second neural network 109. The first neural network 107 analyzes the entire x-ray image and provides a "global" output. This "global" output is a set of scores indicating the probability that the x-ray includes features associated with lung abnormalities, such as lung nodules, based on the analysis of the of the entire x-ray image. Due to the generally large size of chest x-rays, the first neural network may analyze an image of the x-ray at a reduced or down-sampled resolution. This can dramatically improve the efficiency and throughput of the first neural network.

In parallel to the first neural network 107, the second neural network 109 analyzes subsections of the chest x-ray to identify potential features associated with a chronic lung pathology. However, unlike the first neural network, the second neural network analyzes these subsections at, or near-to, the original resolution. The second neural network provides "local" outputs 113. These "local" outputs are sets of scores indicating the probability that a particular x-ray subsection includes features associated with lung abnormalities. The "local" output may also indicate that certain subsections, and thus locations in the x-ray, do not contain a lung abnormality.

Moreover, a full resolution chest x-ray images are between 12- and 16-bit. Thus, at a minimum, the x-ray subsections can include at a minimum 4096 shades of grey. A human, by contrast, can only detect 30 shades of grey. The second neural network can examine the x-ray subsections pixel by pixel to detect minute distinctions grey shading, and thereby detect potential features that could otherwise not be detected by a human technician.

In part, because the neural networks analyze images of different resolutions, they provide distinct score sets. In certain aspects, the "global" output from the first neural network may be a set of scores that represent the probability that the chest x-ray contains lung abnormalities at locations in the x-ray. The "local" output from the second neural network may be a set of scores that represents the probability that a particular subsection or location in the x-ray, includes a lung abnormality. By using both scores, the ML systems of the disclosure can provide a predictive output of whether an x-ray is indicative of lung abnormalities, and the potential locations of those abnormalities.

Although the system 101 only shows the first and second neural networks, additional neural networks can be employed. For example, in certain systems of the invention, a third neural network is used to analyze subsections of the x-ray image, which may be larger than those analyzed by the second neural network and have a resolution between the original resolution and the reduced resolution used in conjunction with the first neural network.

In certain aspects, the third neural network provides an "intermediate" output. This output may be a set of scores indicative of, for example, certain anatomical features such as ribs and/or larger lung abnormalities. By using such a third neural network, lung abnormalities that were identified using the second neural network as separate, individual abnormalities can be resolved into a single large abnormality. In certain aspects, the third neural network may provide an "intermediate" output indicative of the entire size or shape of a potential lung abnormality, while the "local" output is indicative of more detailed features, or "local" for example, the density and texture of a potential lung abnormality.

By using these output scores, the ML systems of the invention can accurately detect lung abnormalities.

The sets of scores from the neural networks are used to provide inputs for an ensemble classifier 115, which creates a predictive output 119 that reports the presence of a lung abnormality at locations in the x-ray image.

The neural networks used in the systems of the disclosure may include object detection algorithms. Objects detected in x-rays or x-ray subsections may indicate the presence of features correlated with a lung pathology. Similarly, the detected objects can include features that should not be considered as associated with a lung pathology by the machine learning system, e.g., rib bones when screening for lung cancer.

The object detection algorithms may include convolutional neural networks (CNN). Exemplary CNNs for object detection in the present disclosure include R-CNN, Fast R-CNN, Faster R-CNN, and YOLO. The object detection algorithms may include or work in concert with a region proposal network. In certain aspects, both the first and second neural networks include an object detection algorithm. ML systems of the disclosure may have more than two neural networks, any of which may include an object detection algorithm.

In certain methods and systems of the invention, the second neural network includes a CNN object detection algorithm and a region proposal network. The second neural network may detect objects in one or more subsections of the x-ray.

Figure 2A:
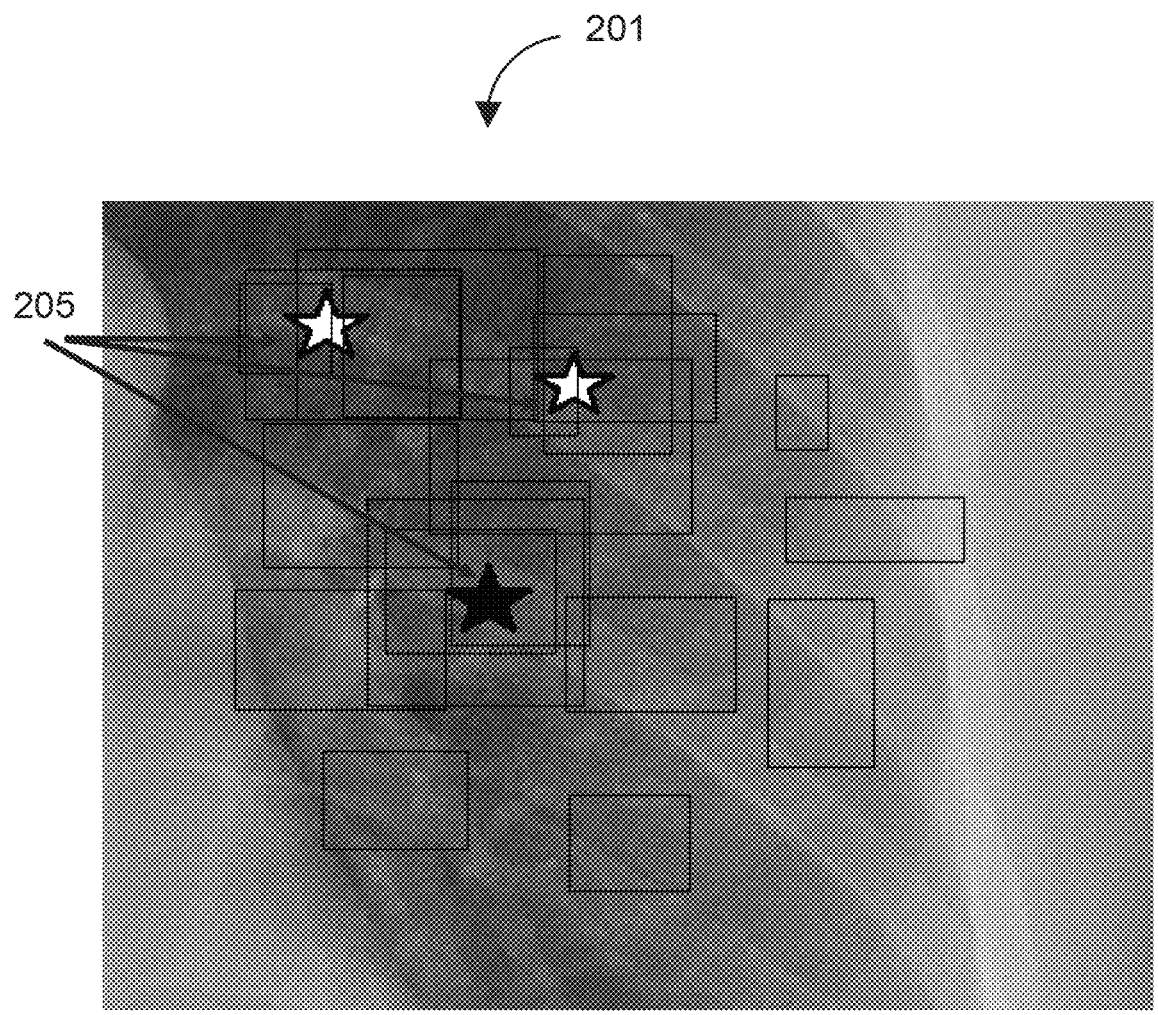
FIG. 2A, FIG. 2B, and FIG. 2C show a chest x-ray used with object detection.
Figure 2B:
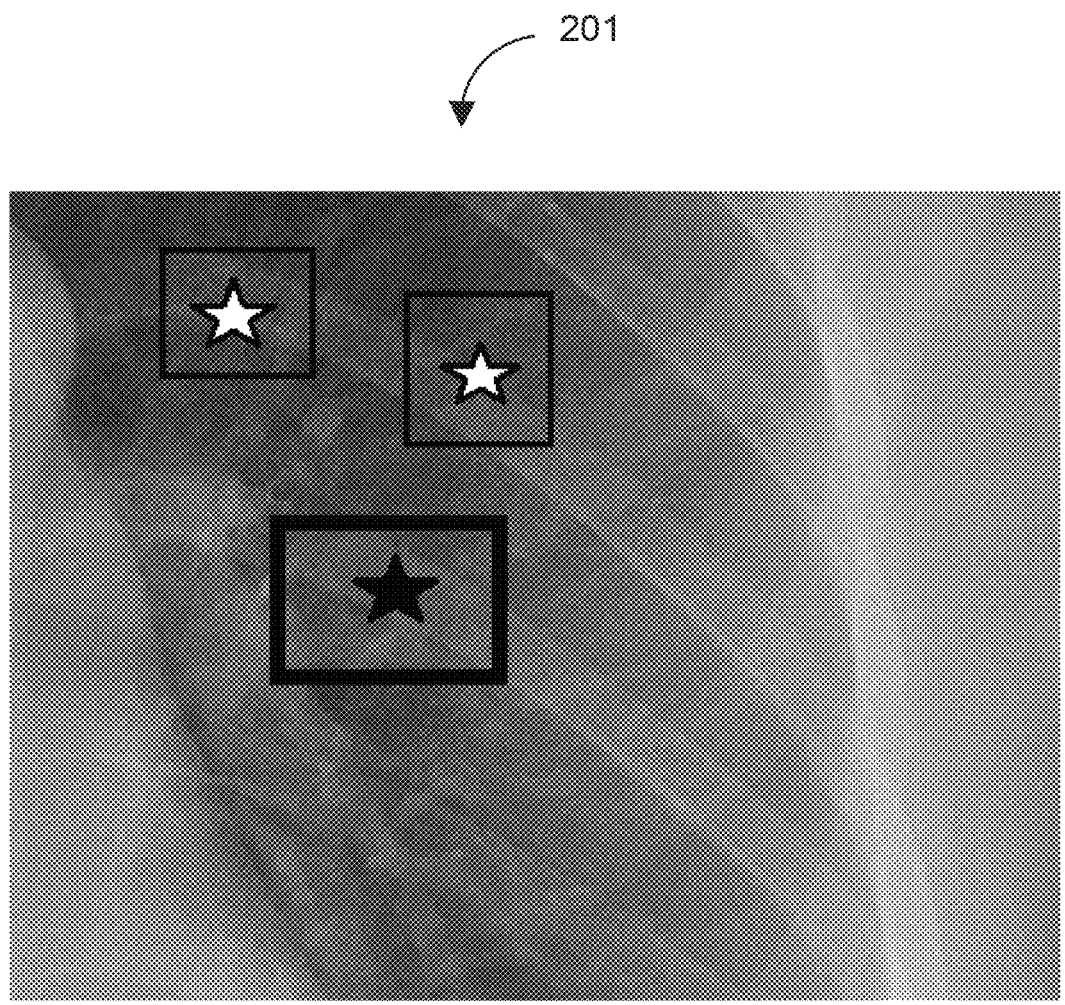
Figure 2C:
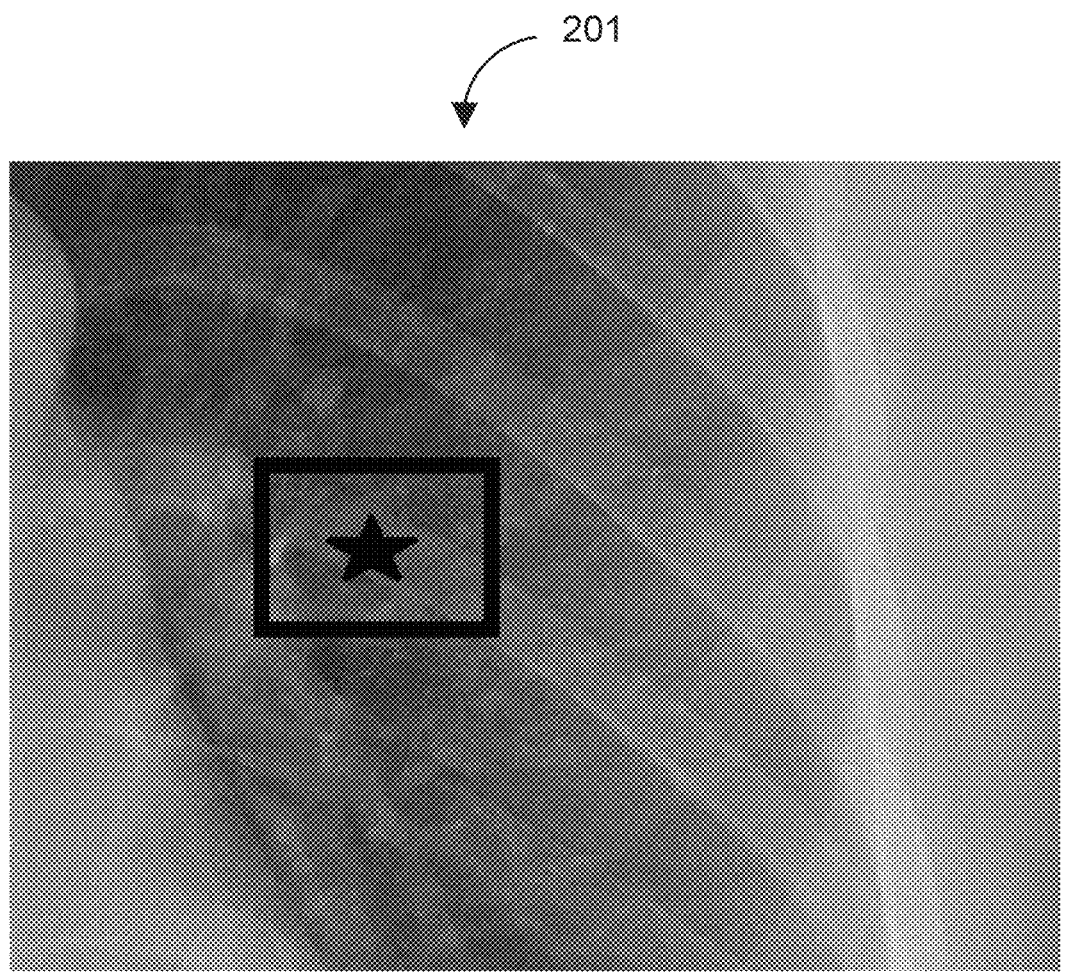

FIGS. 2A-2C provide an exemplary representation of the second neural network detecting an object in a chest x-ray. As shown in FIG. 2A, the second neural network 109 analyzes a subsection of a chest x-ray 201 and searches in regions (shown as black rectangles) provided by the region proposal network to identify potential objects 205. The neural network can assess these regions to determine the probability that they contain an object. As shown in FIG. 2B, the neural network can bound potential objects and assign a confidence value that bound potential objects can be classified as objects. In FIG. 2B, the thicker the lines of the bounding box, the greater confidence value associated with the bound potential object. As shown in FIG. 2C, the neural network may discard potential objects that fail to meet the confidence threshold. The neural network may also create a heatmap of the bounded potential objects and their corresponding confidence values to classify objects using the heatmap.

Figure 3A:
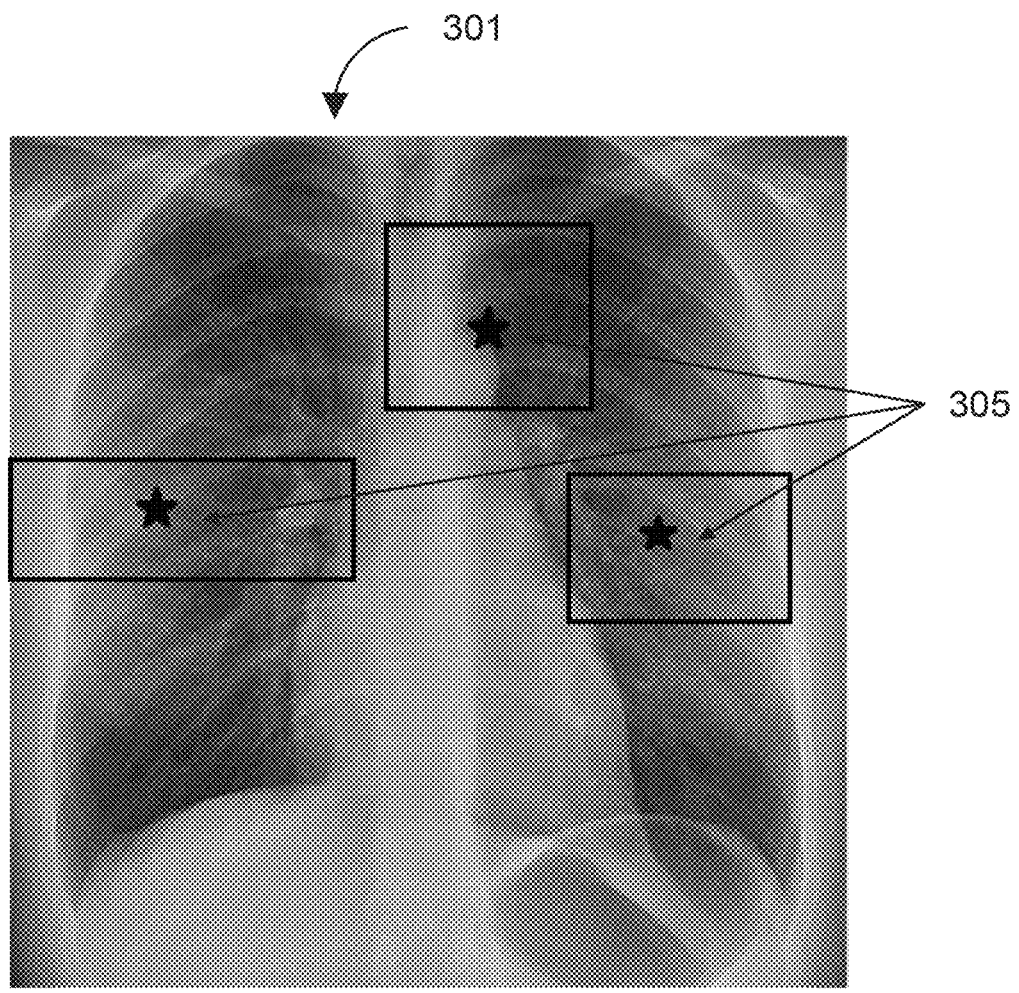
FIG. 3A through FIG. 3B show chest x-ray subsections.
Figure 3B:
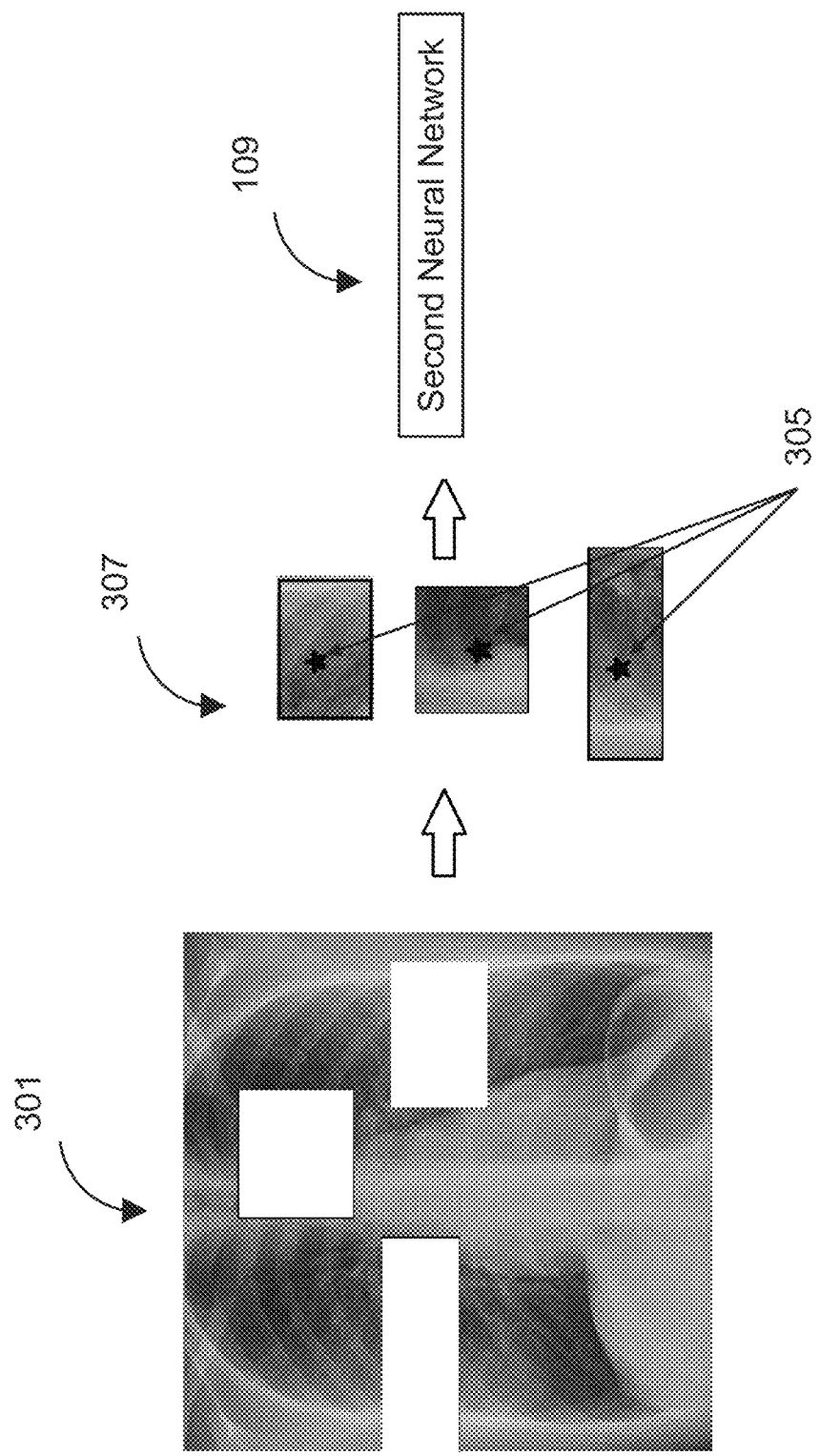

In certain aspects, and as shown in FIGS. 3A-3B, the machine learning system may use a neural network and/or region proposal network to identify and bound potential objects 305 in a chest x-ray 301. As shown in FIG. 3B, the bound regions with the potential objects may be used as the x-ray subsections 307 analyzed by the second neural network 109.

As shown in FIG. 1, the neural networks (107, 109) analyze the chest x-ray (and x-ray subsections) to provide outputs (111, 113) that the ensemble classifier 115 uses to produce a predictive output that an x-ray image contains a lung abnormality. In exemplary ML system 101, the "global" output is a set of scores indicating the probability that the x-ray includes features associated with lung abnormalities based on the analysis of the of the entire x-ray image. The "local" outputs are sets of scores indicating the probability that the x-ray subsections include features associated with lung abnormalities. These output scores may include a classified object detected in the x-ray using a neural network that includes an object detection algorithm. The output scores may further include a confidence value associated with the classified, detected object. Alternatively, or in addition, the neural network(s) will only output a classified object detected in the x-ray with a confidence value above a certain threshold.

Figure 4A:
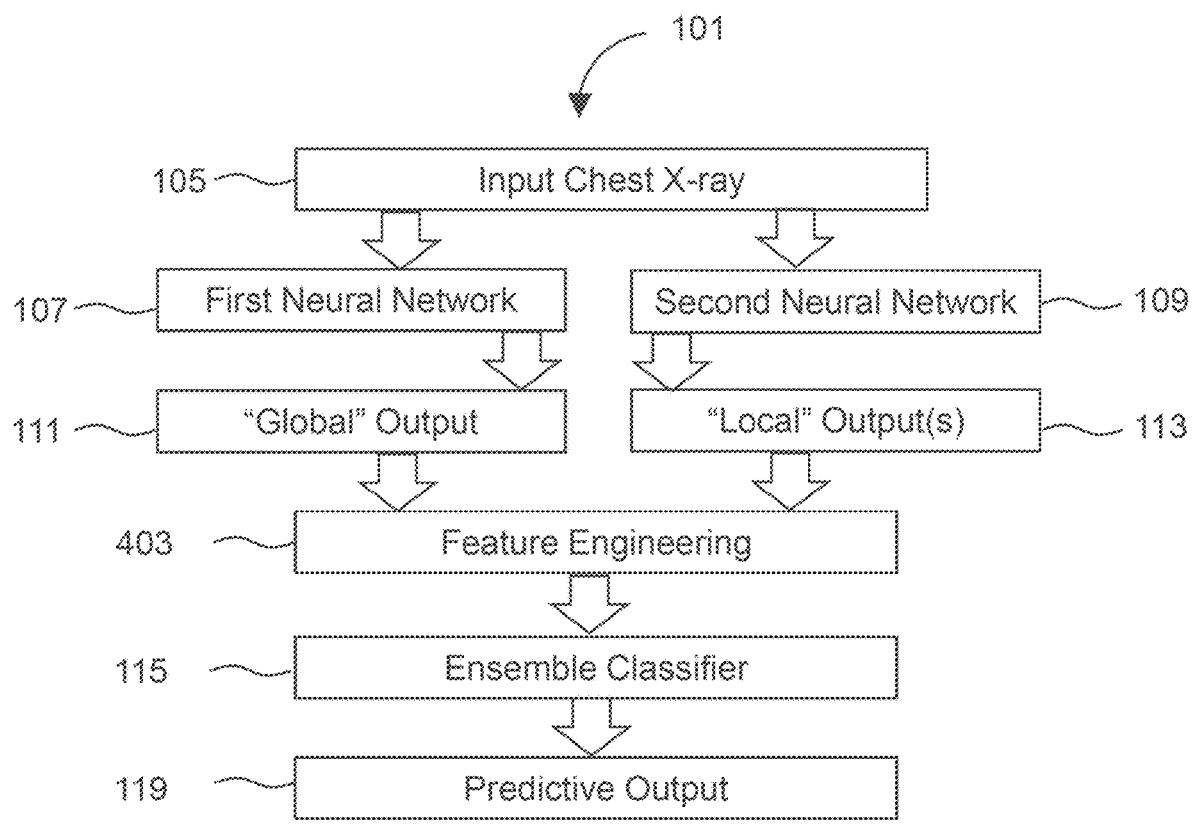
FIGS. 4A-4B show exemplary ML systems of the invention.
Figure 4B:
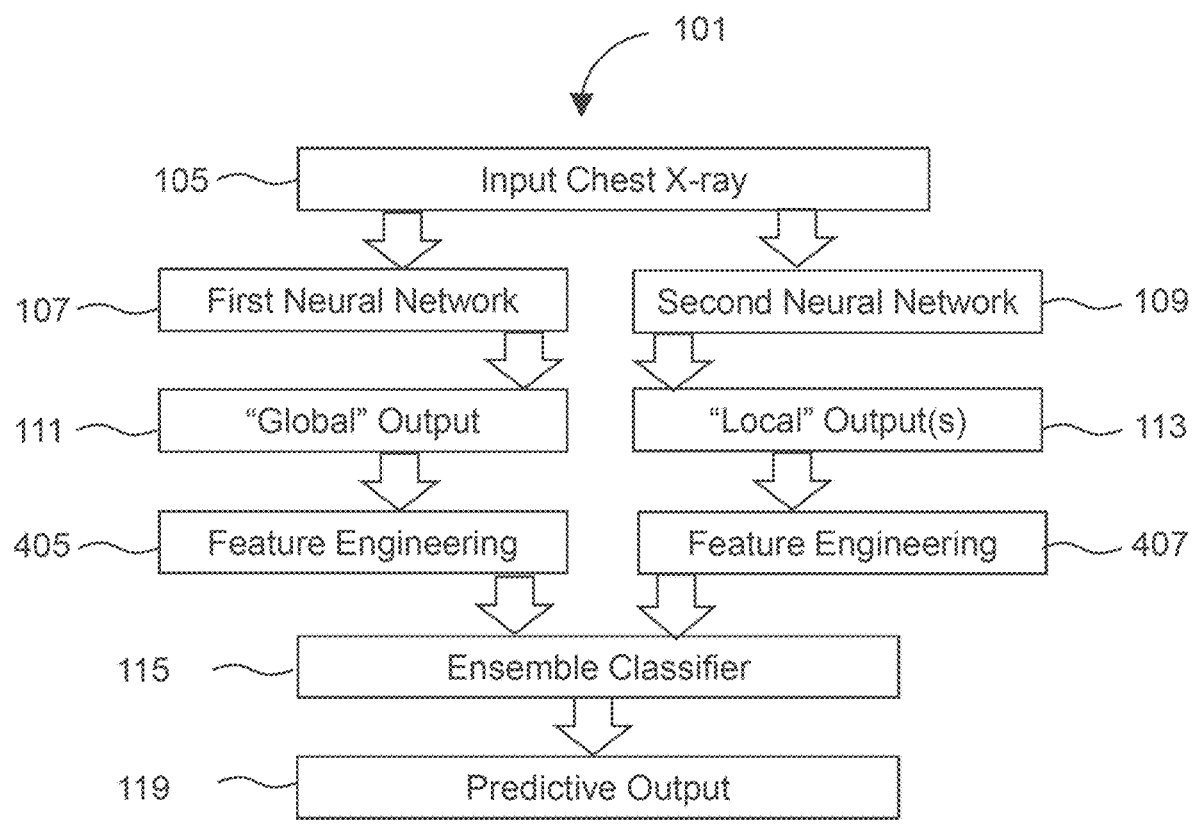

As shown in FIG. 4A, the ML system may include a feature engineering module 403. The neural networks (107, 109) provide outputs (111, 113) to the feature engineering module 403. As shown in FIG. 4B, each neural network may provide its output to a separate feature engineering module (405, 407).

The feature engineering module (403, 405, 407) uses the output scores to create features in the x-ray that can be analyzed by the ensemble classifier. The feature engineering module may compare or combine the output scores from the neural networks, for example, the "global" and "local" outputs in exemplary system 101. The created features may correspond to features in x-ray image indicative of a certain lung pathology. Further, the feature engineering module may dismiss potential features identified by the neural networks, because, for example, the neural networks disagree about whether a particular feature exists in the x-ray.

As shown in FIGS. 4A-4B, the feature engineering module provides the created features as inputs to the ensemble classifier 115. The ensemble classifier may include, for example, a random forest.

Figure 5:
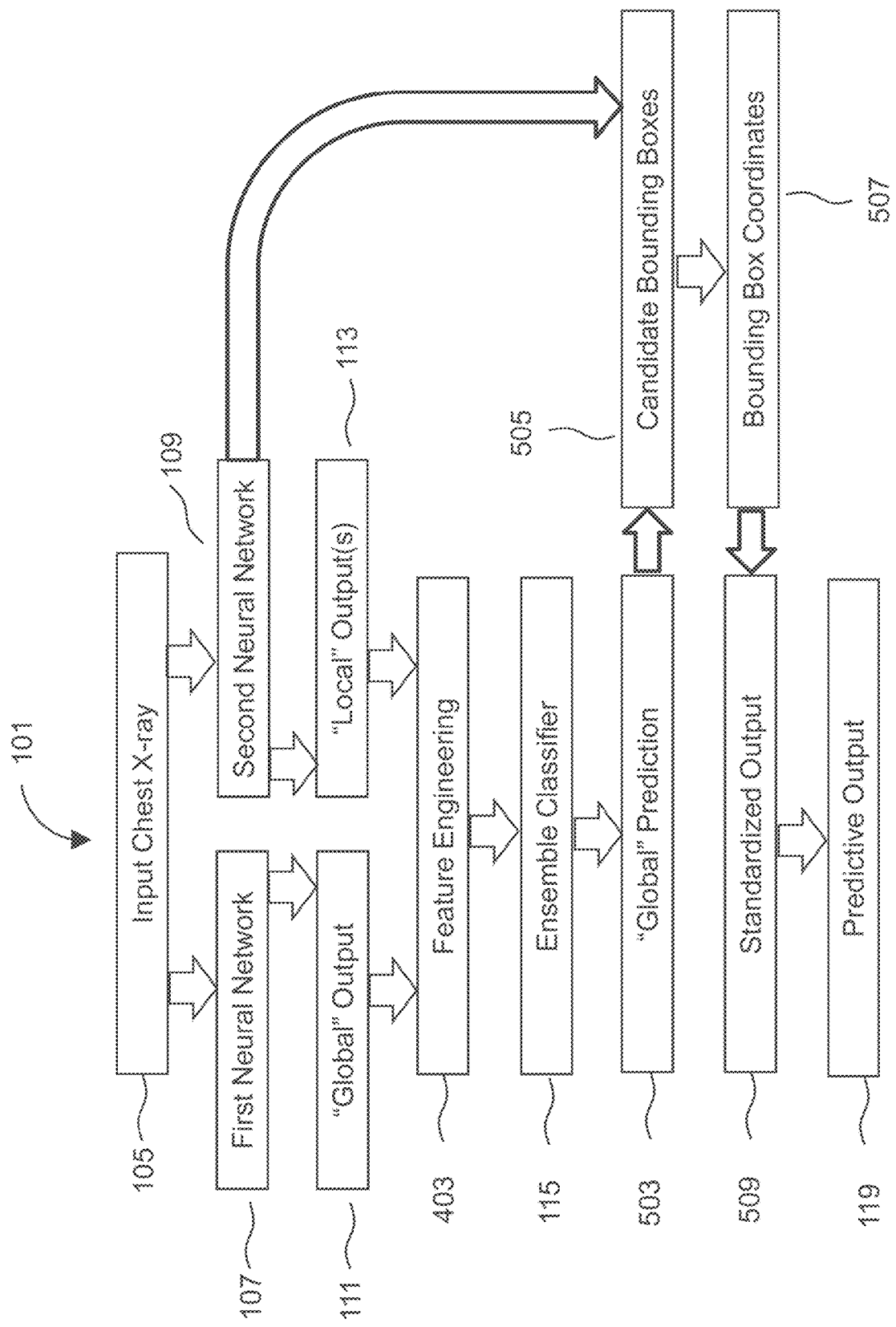
FIG. 5 shows an exemplary ML system of the invention.

As shown in FIG. 5, in certain aspects, the ensemble classifier 115 of the ML system may produce a "global" prediction 503. This prediction may indicate that the x-ray image contains lung abnormalities. The "global" prediction 503 may also include whether abnormalities can be found in certain subsections of the x-ray image analyzed by the second neural network contain (or do not contain) an abnormality. Thus, for example, the "global" prediction may indicate that the x-ray contains lung nodules, and that they are located within certain x-ray subsections.

As also shown in FIG. 5, the abnormalities from the "global" prediction 503 are bound by candidate bounding boxes 505. The bounding boxes may correspond to the x-ray subsections analyzed by the second neural network 109. Alternatively, or in addition, the bounding boxes may correspond to the bounding boxes provided by an object detection algorithm and/or region proposal network of the second neural network. The candidate bounding boxes are associated with coordinates, i.e., bounding box coordinates 507, on the x-ray image. The bounding box coordinates can then be used to provide a standardized output 509, which is used to provide the predictive output 119.

Figure 6:
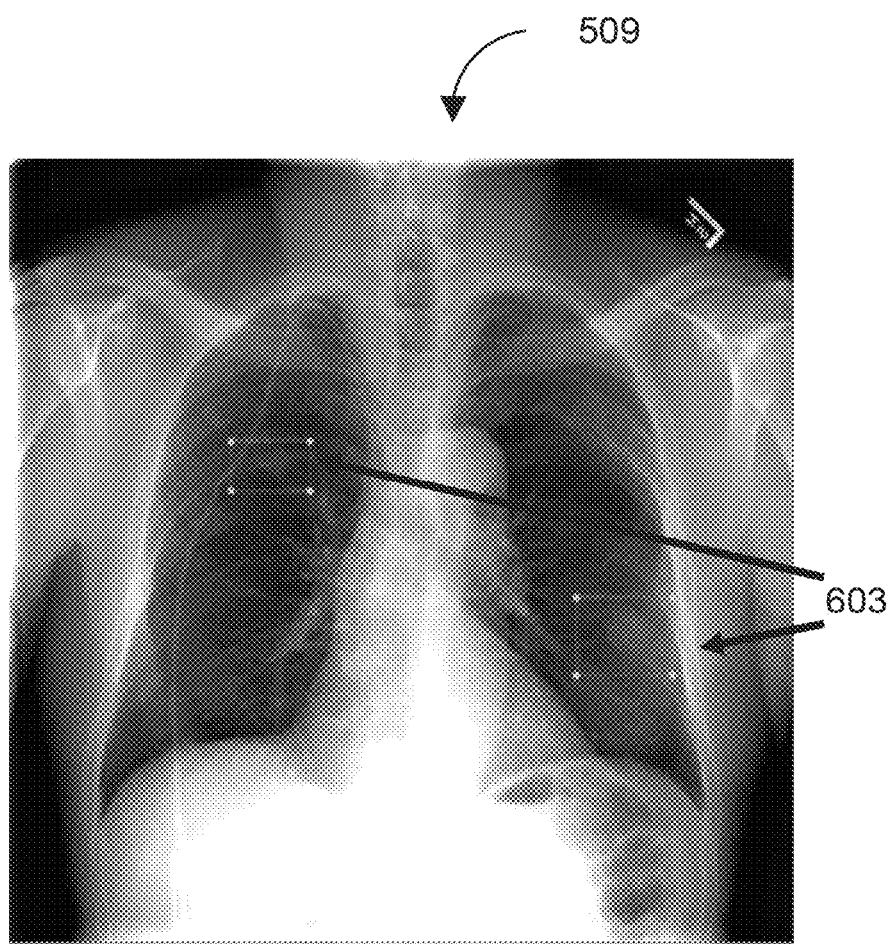
FIG. 6 shows an exemplary standardized output.

FIG. 6 provides an exemplary standardized output 509. The bounding box coordinates 507 have been used to create visual bounding boxes 603 on the x-ray image. This standardized output 509 can be used and analyzed by a human technician or another ML system. The standardized output can also include image adjustments, corrections, and resizing to ensure that downstream analysis or use of the image is free of any potential artifacts inherent to certain images. The standardized output may also include alterations to ensure compatibility with certain software packages, tools, ML systems, and archiving systems, such as picture archiving and communication systems (PACS).

Figure 7:
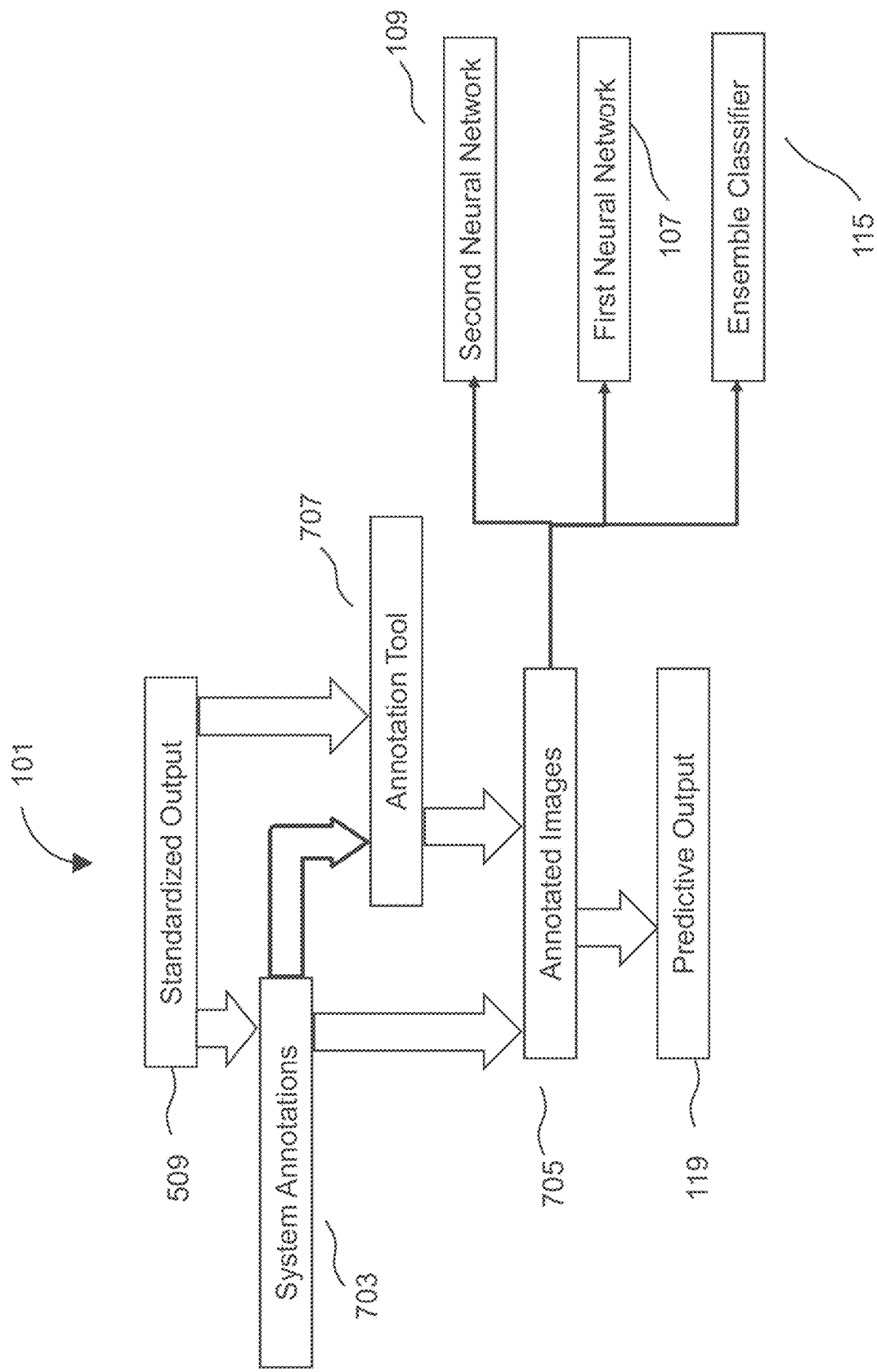
FIG. 7 shows a portion of the exemplary ML system of the invention.
Figure 8:
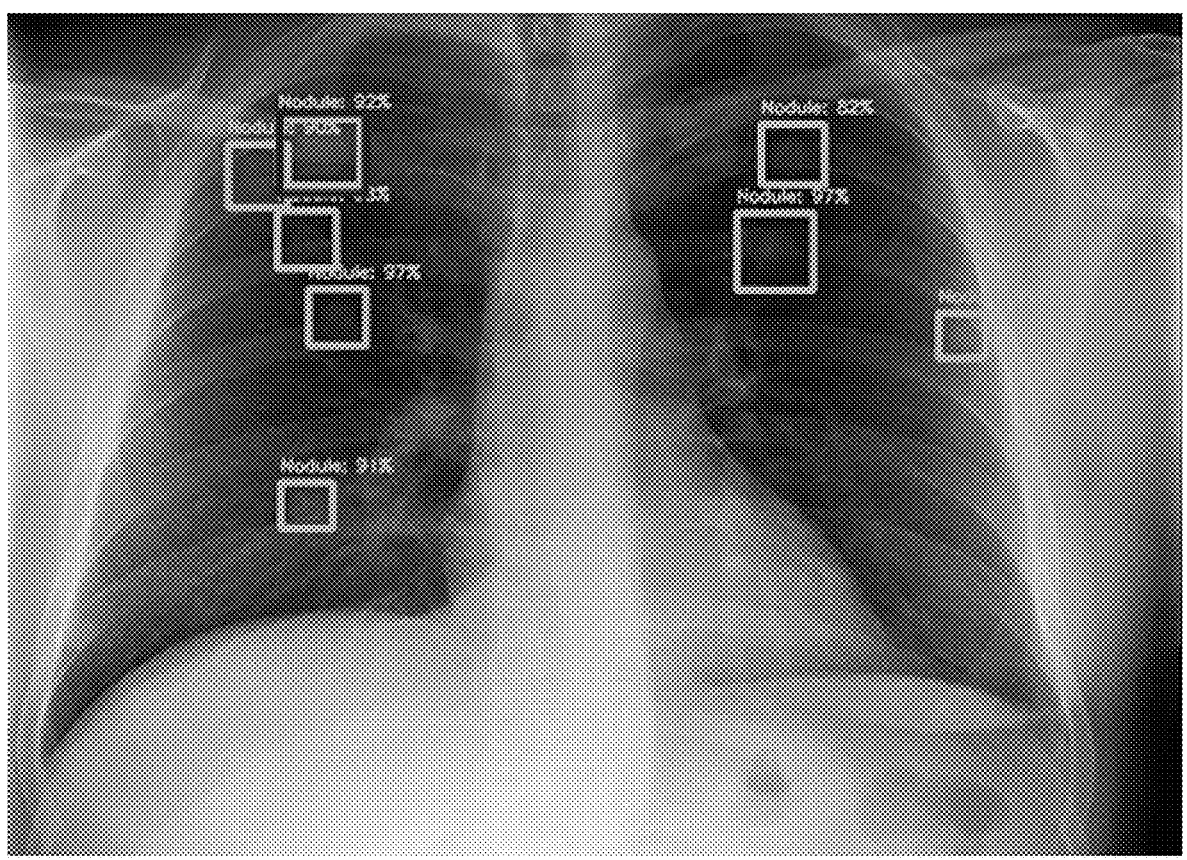
FIG. 8 shows an exemplary annotated chest x-ray image, in which the ML system identified potential lung nodules, labeled them on the x-ray image, and provided a confidence value associated with the potential lung nodules.

As shown in FIG. 7, the ML system can use the standardized output 509 and annotate the images with system annotations 703 to provide annotated images 705. FIG. 8 provides an exemplary annotated image, in which the system identified potential lung nodules, labeled them on the x-ray image, and provided a confidence value associated with the potential lung nodules.

Figure 9:
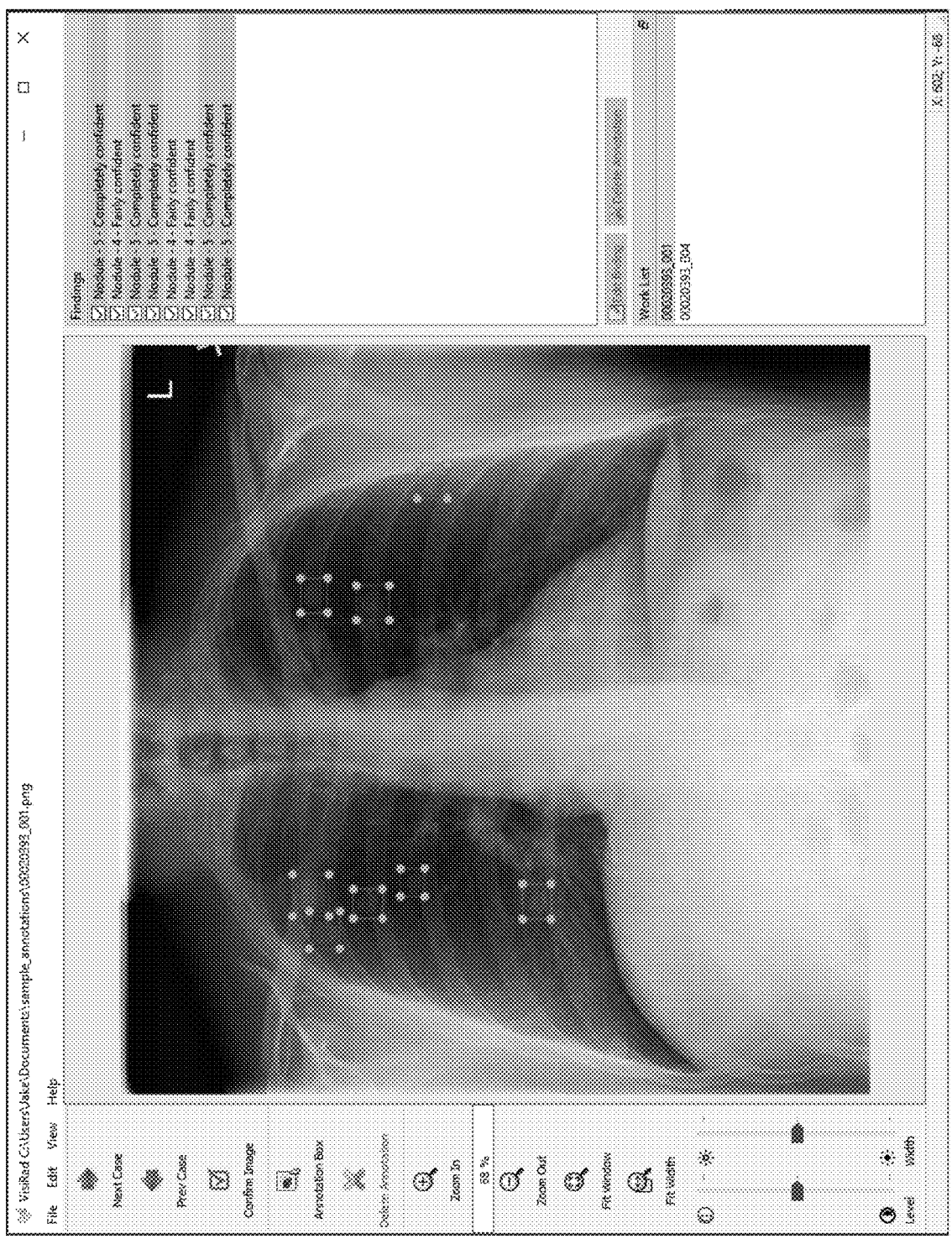
FIG. 9 shows an exemplary interface of an annotation tool.

As also shown in FIG. 7, the standardized output may be manipulated by a human technician using an annotation tool 707. FIG. 9, shows an exemplary interface of an annotation tool 707. As shown, a human technician can review the standardized output and/or an image annotated with system annotations. The technician can use the tool to annotate the image and/or accept or reject system annotations. As shown in FIG. 7, the annotated images can be used to provide the predictive output. Moreover, the annotated images can be used to train the ML system, including the neural networks (109, 107) and the ensemble classifier 115. Images can also be annotated in a longitudinal manner. For example, as a patient's disease progresses or regresses, that information can be used to annotate an image, and be used to train the ML system.

The present invention also includes methods of training the machine learning systems. In certain aspects, various components of the ML systems include machine learning components, for example, the neural networks (and associated object detection algorithms), the feature engineering module(s), and the ensemble classifier. Each of these components can be trained in accordance with the present invention.

In certain aspects, the present invention includes training the ML systems using training data sets that include chest x-ray images from patients with known pathologies, clinical outcomes, diagnoses, and/or identified lung abnormalities, such as lung nodules. This allows the ML systems to identify features in the chest x-rays and correlate the features with the known pathologies, clinical outcomes, diagnoses, and/or identified lung abnormalities.

However, the inventors discovered that solely training an ML system using chest x-rays led to errors, such as missing lung nodules in chest x-rays, and an error rate of approximately 20%-50%. This is due, in part, to the nature of the chest x-rays in the training data. An estimated 90% of mis-diagnosed lung cancer cases are due to radiologist error when analyzing chest x-rays. (Del Ciello et al, "Missed lung cancer: when and why?", Diagn Interv Radiol, 23(2): 118-126 (2017)). It is often difficult for radiologists to distinguish lung abnormalities from other features, such as bones, pulmonary vessels, and other anatomical structures found in chest radiographs. Furthermore, the human eye is only capable of distinguishing approximately 30 different shades of grey. Many lung abnormalities in chest x-rays are thus entirely indistinguishable to the human eye. Accordingly, ML systems trained solely using chest x-rays and their associated patient outcomes and diagnoses are trained using data sets that contain human error. This error can extend through the operation of such an ML system.

To reduce or eliminate this error, the present inventors included in training data sets CT scans and associated data, such as patients' known pathologies, diagnoses, and clinical outcomes. The CT data can be used to ground truth features detected in x-ray images that are correlated with a particular lung abnormality. Bringing this highly accurate CT scan data into the training sets can markedly improve the accuracy of the ML systems.

The present Inventors also discovered that the CT scan training data, when used in a particular manner, can further improve the accuracy of the present ML systems. The ML systems can be trained or use data that correlates features in CT scans to known patient diagnoses, clinical outcomes, and pathologies. The ML systems are then trained to associate features in chest x-rays to the features in CT scans. In this way, the ML systems of the present invention can link features in x-rays with accurate feature-to-abnormality correlations in the CT scan data. This training data can replace or supplement potentially inaccurate training directly correlating x-ray features to lung abnormalities.

By employing this training regime, the present Inventors were able to train ML systems until they were able to detect lung nodules in x-ray images with an area under the curve (AUC) of true positives over false positives ≥0.74, which surpasses the performance of an unaided radiologist. Moreover, the ML systems of the invention can be further trained, either with or without a human-in-loop to improve the accuracy of the ML system. In certain aspects, the ML systems of the invention can achieve an AUC of true positive over false positives of at least about 0.74, 0.76, 0.80, 0.84, 0.85, 0.90, 0.95, 0.97, 0.98, 0.99, or between 0.99 and 1. In certain aspects, the ML systems can be trained until they obtain an AUC of 0.74, at which time they are used to analyze patient x-rays. The systems can be further trained while used to analyze patient x-rays to improve their accuracy. In certain aspects, the ML system can be trained until it attains an AUC of true positive over false positives of at least about 0.74, 0.76, 0.80, 0.84, 0.85, 0.90, 0.95, 0.97, 0.98, 0.99, or between 0.99 and 1.

The present Inventors also made the surprising discovery that the ML systems can be further improved if, prior to training the systems using clinically relevant data (e.g., chest x-rays and CT scans), the ML systems were trained with images that did not contain lungs. By initially training the system with random images, the ML systems were more accurate than systems trained solely using clinically relevant data.

In order to train the ML systems of the present invention, relevant training data must be obtained. This data can include, for example, chest x-rays, CT scans, PET-CT scans, and associated known patient pathologies, diagnoses, and/or patient clinical outcomes. In certain aspects, the ML systems are trained using training data that includes chest x-rays and CT scans associated with known pathology results, patient diagnoses, and/or clinical outcomes. The chest x-rays may also be associated with known pathology results, patient diagnoses, and/or clinical outcomes. These associations may be annotated on the CT scans and chest x-rays.

In certain aspects, the training data includes chest x-rays associated with known pathology results, patient diagnoses, and/or clinical outcomes. The training data also includes CT scans from a subset of the patients that provided the chest x-rays.

Generally, ML systems have increased accuracy when trained using large data sets, and can continually improve with additional training data. In order to obtain this volume of data, it must come from distributed sources, such as various hospitals and research institutions. However, the training data x-rays, CT scans, and the like are cultivated from individual patients. Therefore, to assure patient confidentiality and privacy, and in order to comply with relevant regulations such as the Health Insurance Portability and Accountability Act (HIPAA), confidential patient data should not leave the various hospitals and institutions.

Figure 10:
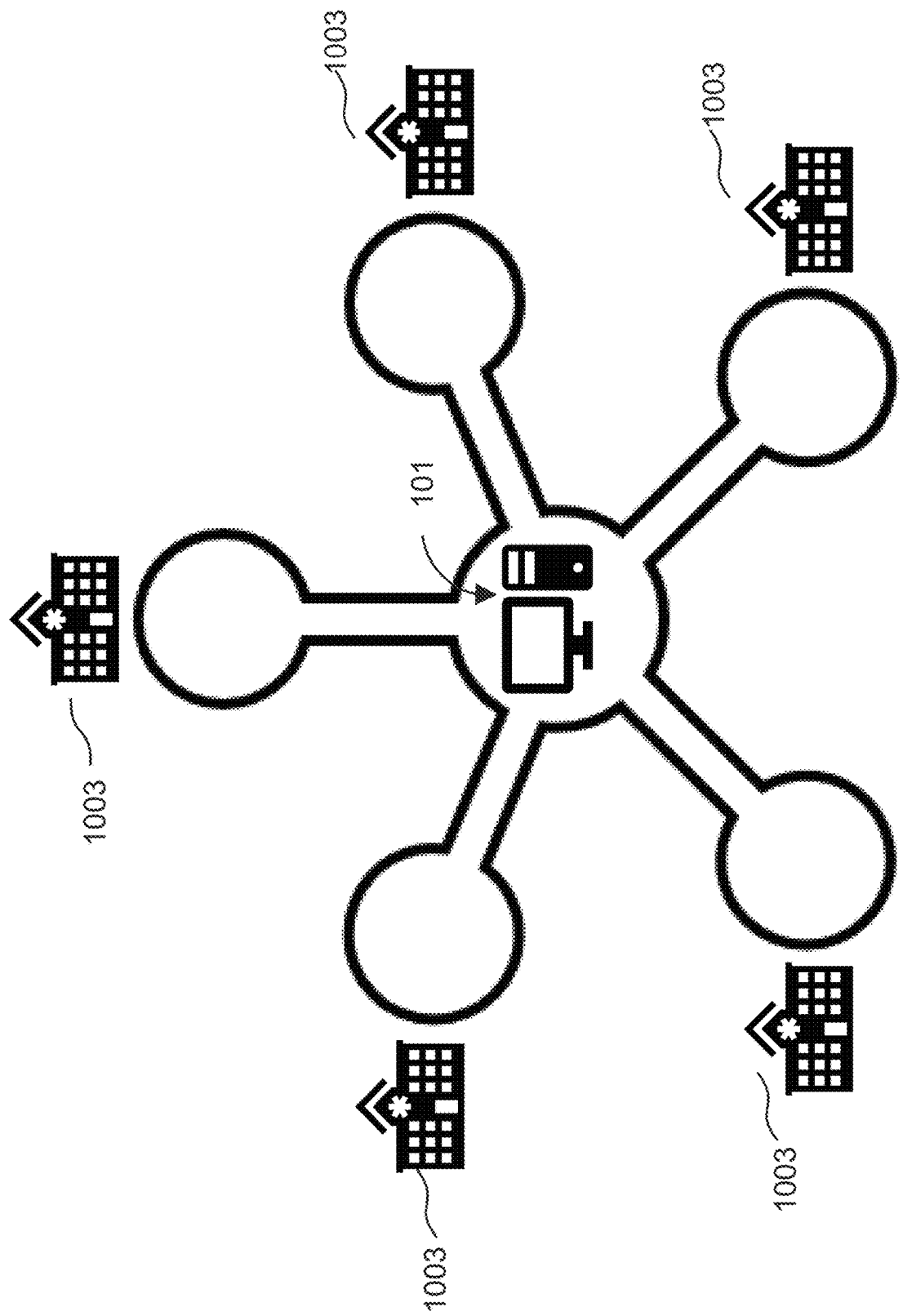
FIG. 10 shows an exemplary ML system that receives data from distribute sources

FIG. 10 shows the ML system 101 connected to various locations 1003 that have the required training data. These locations 1003 are separated from the ML system by time and/or geography.

Figure 11:
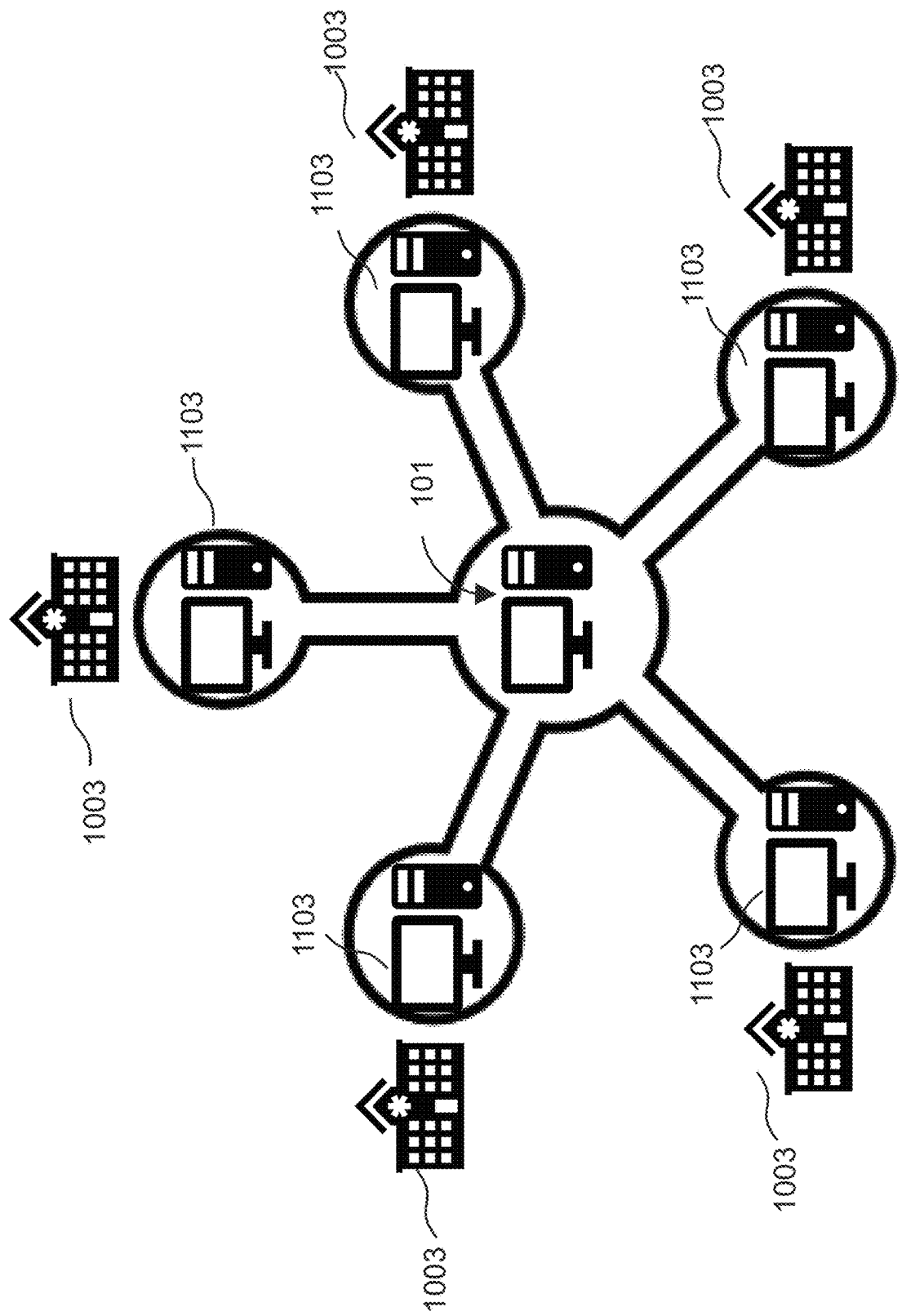
FIG. 11. shows an exemplary ML system that receives data from ML subsystems at distributed sources.

As shown in FIG. 11, distributed ML subsystems 1103 can be emplaced at these various locations and trained using local data. The ML subsystems 1103 may be connected to, or receive data from, data stores at the various locations. These data stores may, for example, be picture archiving and communication systems (PACS). These subsystems 1103 can be computer hardware systems sent to the various locations, which include the ML subsystem architecture. Advantageously, this provides a gap between the data archives at a location and the ML system 101. Alternatively, the ML subsystems can be hosted on, or integrated into, computer systems at the various locations.

The trained ML subsystem 1103 can update the central ML system, for example, using a federated learning model. By using such an arrangement, the ML systems of the invention can be trained using data from distributed sources, while ensuring that confidential patient data does not leave a hospital or other research institution. Alternatively, or in addition, the ML subsystems 1103 may obtain data, such as chest x-rays and CT scans, scrub them of all private or confidential data, and send them to the ML system 101 or another central image repository.

Moreover, in certain aspects, the ML system 101 or subsystems 1103 can standardize data from various locations to eliminate biases or artifacts attributable to different instruments, e.g., CT scanners from different manufacturers, which may be used under diverse imaging conditions and/or parameters.

In certain aspects, the ML system 101 and/or subsystems 1103 can be used to develop masks that can be applied to data, such as x-rays and CT scans, from different instruments, operating conditions and/or parameters. A different mask can be applied, for example, to data from different instruments. Applying the masks to the data from the different instruments standardizes the data obtained from those instruments.

In certain aspects, the ML system 101 and/or subsystems 1103 obtain diverse CT scans from different CT scanning instruments at the various data locations 1003. The ML system 101 and/or subsystems 1103 use the diverse scans to create standardized CT scans. The standardized CT scans are free of biases and artifacts found among the diverse CT scans, which are attributable to the different CT scanning instruments and/or conditions or parameters under which they operate. Moreover, standardized scans may be resized and/or have their resolutions altered from the original, diverse CT scans. The standardized CT scans can be used in the ML systems of the invention to ground truth features identified in x-ray images.

In certain aspects, the ML subsystems 1103 obtain data from diverse CT scans, and use the data to reconstruct the scans into standardized CT scans. The ML subsystems 1103 may recognize certain characteristics in CT scans attributable to particular instruments and/or operating conditions and parameters. Upon recognizing such characteristics, the ML subsystems 1103 may create standardized CT scans from the scans with the recognized characteristics. Additionally, in certain aspects, when reconstructing the scans, any confidential information contained in the diverse CT scans can be removed. The ML subsystems 1103 can reconstruct the scans using deep learning reconstruction. In certain aspects, the ML subsystem 1103 include a CNN algorithm, which is used to reconstruct the scans. The ML subsystems may form one or more generative adversarial networks that are used to create the standardized scans.

In certain aspects, the standardized CT scans may be standardized to a particular instrument and/or operating conditions and parameters. Thus, the reconstructed scans remove any characteristics attributed to the original instrument, conditions, and parameters, and add characteristics attributed the particular instrument and/or operating conditions and parameters.

Figure 12:
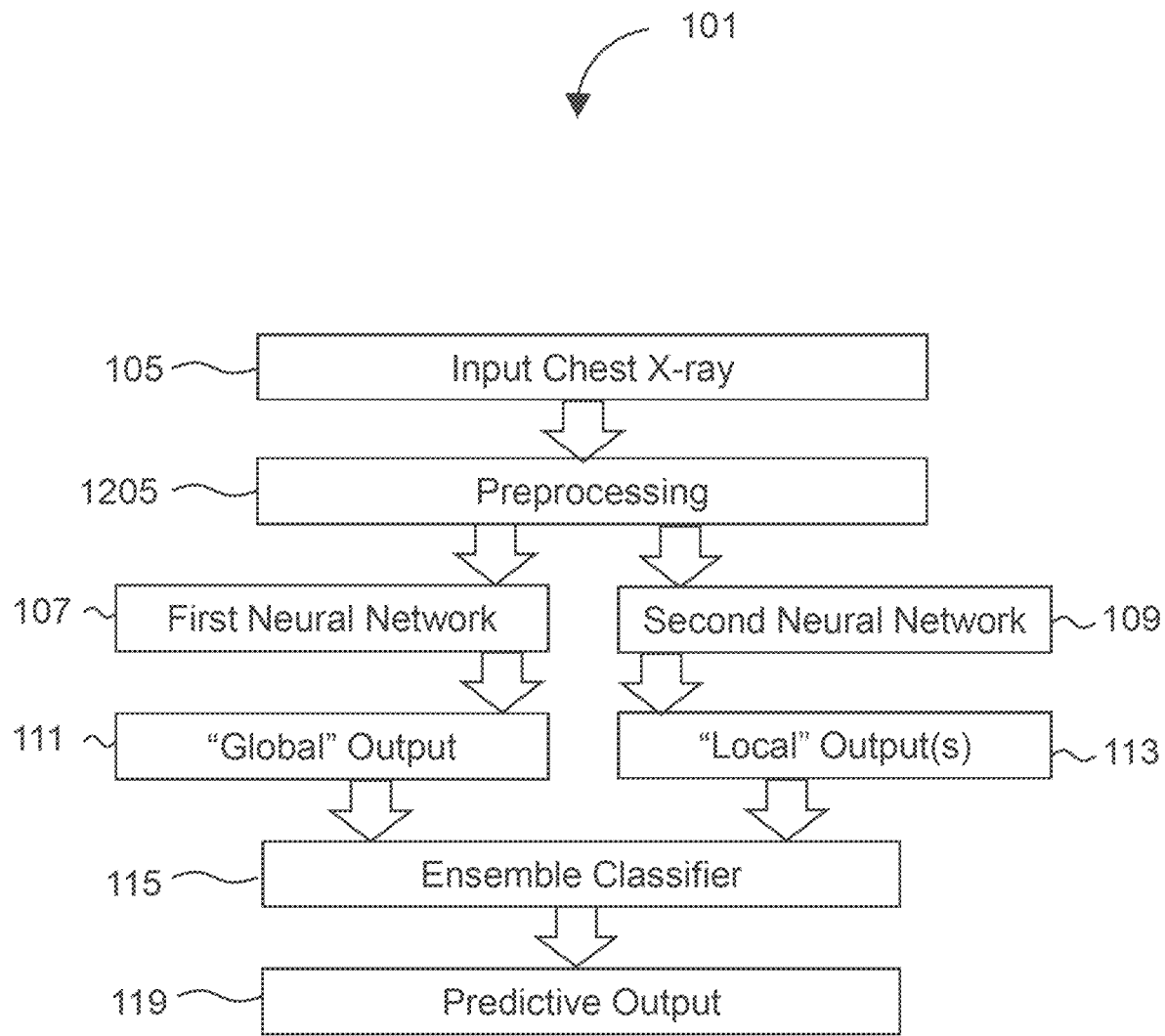
FIG. 12 shows an exemplary ML system of the invention.

As shown in FIG. 12, the ML system 101 may include preprocessing 1205 steps and/or modules before data from an x-ray is provided to the neural networks (107, 109). Processing is a key step, especially with image data as ML inputs. ML can be used in analyzing, for example, x-ray images. This may include a "global" and "local" analysis of images to, for example, quantify areas with certain features or potential objects. However, in order for the ML system to accurately assess these features, preprocessing may be required.

Figure 13:
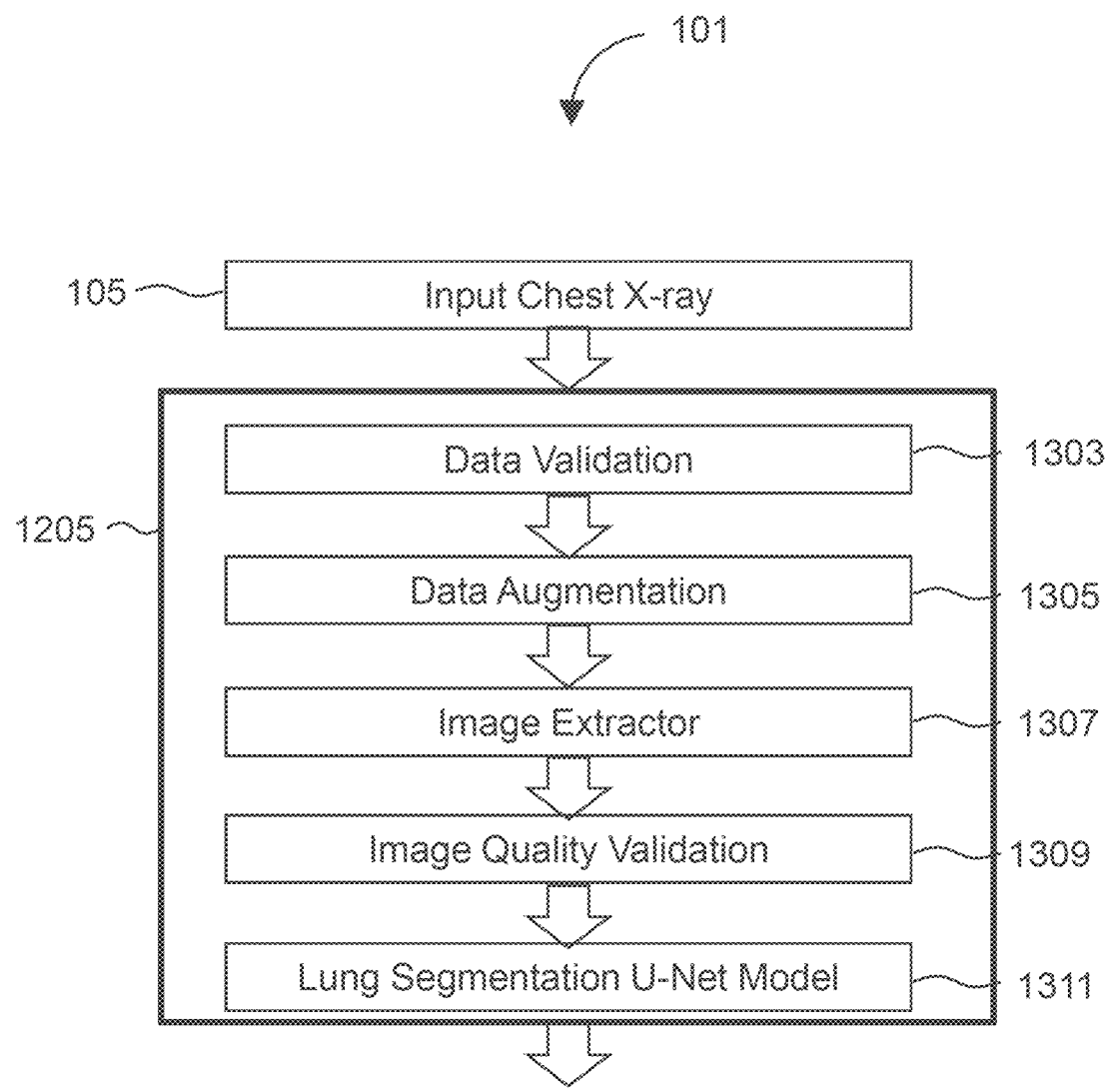
FIG. 13 shows preprocessing used in the ML system of the invention.

As shown in FIG. 13, preprocessing may include data validation 1303, data augmentation 1305, an image extractor 1307, image quality validation 1309, and a lung segmentation U-Net model 1311.

Data validation 1303 may include, for example, ensuring that a data file containing the chest x-ray is complete, including any annotations, and uncorrupted. This step may also ensure that the data entering the ML system does not include any private or confidential information. Data validation may also assure that the data entering the ML system is in a correct and/or standardized format such that it can be analyzed the ML system.

Data augmentation 1305 may include, for example, annotating an x-ray. Annotations can be made by the machine learning systems and/or humans-in-loop. Annotations can include additional data that is associated with known pathologies. This additional data may include, for example, bioassay data (e.g., genomic and expression data) patients' ages, sex, ethnicities, comorbidities, clinical outcomes, medical treatments and history, and patients' familial histories. Data augmentation 1305 may also include a human-in-loop annotating particular features in the x-ray. The ML system 101 can be trained to correlate this additional data with features in x-ray images, which can improve the predictive accuracy of the system. A human-in-loop may also annotate images such the ML system 101 focuses on and/or disregards certain features or areas in the x-ray image.

Data augmentation 1305 may also include transforming the data, which may have been obtained from particular instruments, locations, times, and/or operating parameters, into a standardized format.

The image extractor 1307 extracts the chest x-ray image from a data file such that it can be analyzed by the neural networks. In certain aspects, the image extractor may extract a chest x-ray image and reduce or downsize the resolution to provide the whole x-ray image analyzed by the first neural network. Similarly, the image extractor may extract a chest x-ray image and further extract one or more subsegments from it for use by the second neural network.

The image quality validation model 1309 may, for example, assess the resolution of extracted images to assure they are appropriate for analysis by the neural networks. This is particularly important when the ML system includes CCNs, as many require that images fit within the CCNs' fixed window sizes. In certain aspects, the image quality validation model 1309 may mask or remove unwanted radiographic annotations on the image, for example, the initials of a technician who obtained the chest x-ray.

The image quality validation model 1309 may also include edge detection algorithms. Such algorithms can identify, for example, extreme changes in brightness, saturation, and discontinuities in an image. Using edge detection algorithms, the image quality validation model can detect portions of x-rays that are irrelevant for analysis. For example, chest x-rays often include an entire torso, portions of the head and neck, arms, shoulders, and empty space surrounding the torso. The edge detection algorithms can identify and remove these irrelevant features, which reduced the computational burden of analyzing the image.

The lung segmentation U-Net model 1311 can be used to identify lungs in a chest x-ray image. In certain aspects, the lung segmentation U-Net model 1311 applies a mask to the chest x-ray, which identifies the areas of the x-ray that contain the lungs. Similar to the edge detection algorithms, once the lungs are identified in the x-ray, irrelevant portions of the x-ray can be disregarded by the ML system 101.

Figure 14:
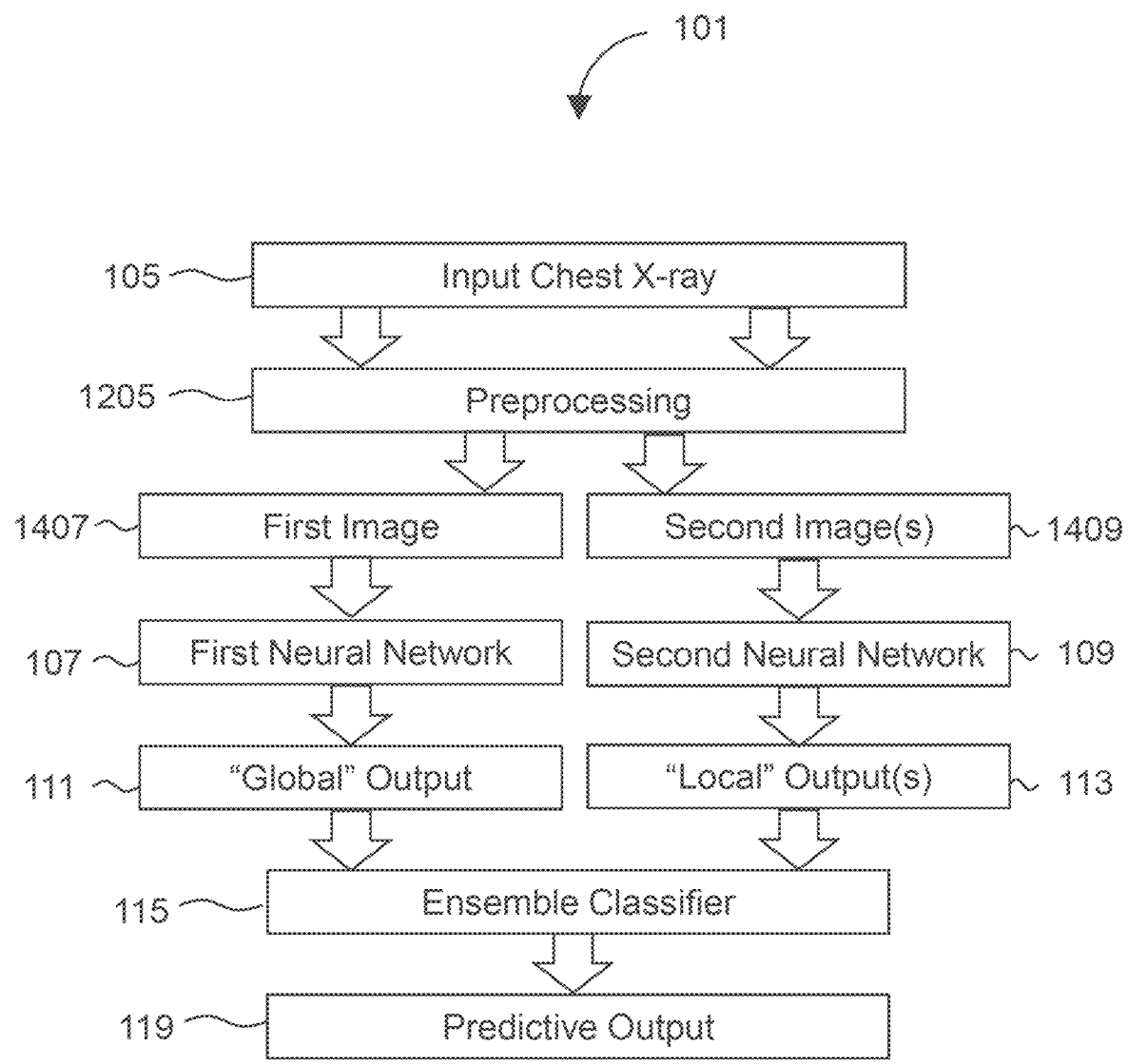
FIG. 14 shows an exemplary ML system of the invention.

As shown in FIG. 14, after preprocessing a first image and a second image(s) are created, with the first used as an input for the first neural network, and the second for the second neural network.

The ML systems of the invention can analyze chest x-rays from a subject to provide predictive outputs 119. Predictive outputs may include signature features correlated with certain types of conditions, such as long nodules in lung cancer. Predictive outputs may be used to assess disease severity. For example, the methods and systems of the invention can assess the severity of a subject's lung cancer and provide predictions regarding the risk of metastasis, recurrence, or residual risk. The outputs may also provide predictions about whether a particular lung abnormality is benign, at-risk, or indicative of cancer. The outputs may provide predictions that classify a cancer type and/or stage a cancer.

Predictive outputs may be longitudinal. Longitudinal outputs may be outputs for the same patient or patient population over time, and updated based upon additional data. Additional data may include, for example, bioassay data (e.g., sputum cytology or genomic information) patients' ages, sex, ethnicities, comorbidities, clinical outcomes, medical treatments and history, and patients' familial histories. Additionally, the lungs of a subject may be monitored at several time points, e.g., by obtaining additional chest x-rays, and analyzed by an ML system of the invention to provide continual predictive outputs.

Predictive outputs may be based upon threshold values. Threshold values may be created by ML models or by humans. ML models may be used to provide predictive outputs for various treatment options for particular patients or patient populations.

The methods and systems of the invention can be used provide predictive outputs for relative treatment efficacies, and any benefit of further monitoring or additional screening (e.g., how often the patient should have lung nodules analyzed). For example, the lungs of a subject may be monitored at several time points, e.g., by obtaining additional chest x-rays, and analyzed by an ML system of the invention to provide continual predictive outputs.

Once lung nodules are detected the ML system, the system can provide predictive outputs that, for example, classify the nodule as a tumor, benign, and/or malignant. The predictive outputs may include an assessment of nodule progression, volumetric sizing, nodule etiology, and/or nodule histology.

The predictive outputs can be used as stand-alone predictions of a particular pathology in a subject, such as lung nodules indicative of lung cancer. Alternatively or additionally, the predictive outputs can be used to assist a human technician analyzing an x-ray from a subject. Advantageously, a human technician can confirm or reject predictions made by an ML system of the invention. An affirmation or rejection of an ML system's predictions can be incorporated into training data sets used to improve the ML system or train a new system.

Figure 15:
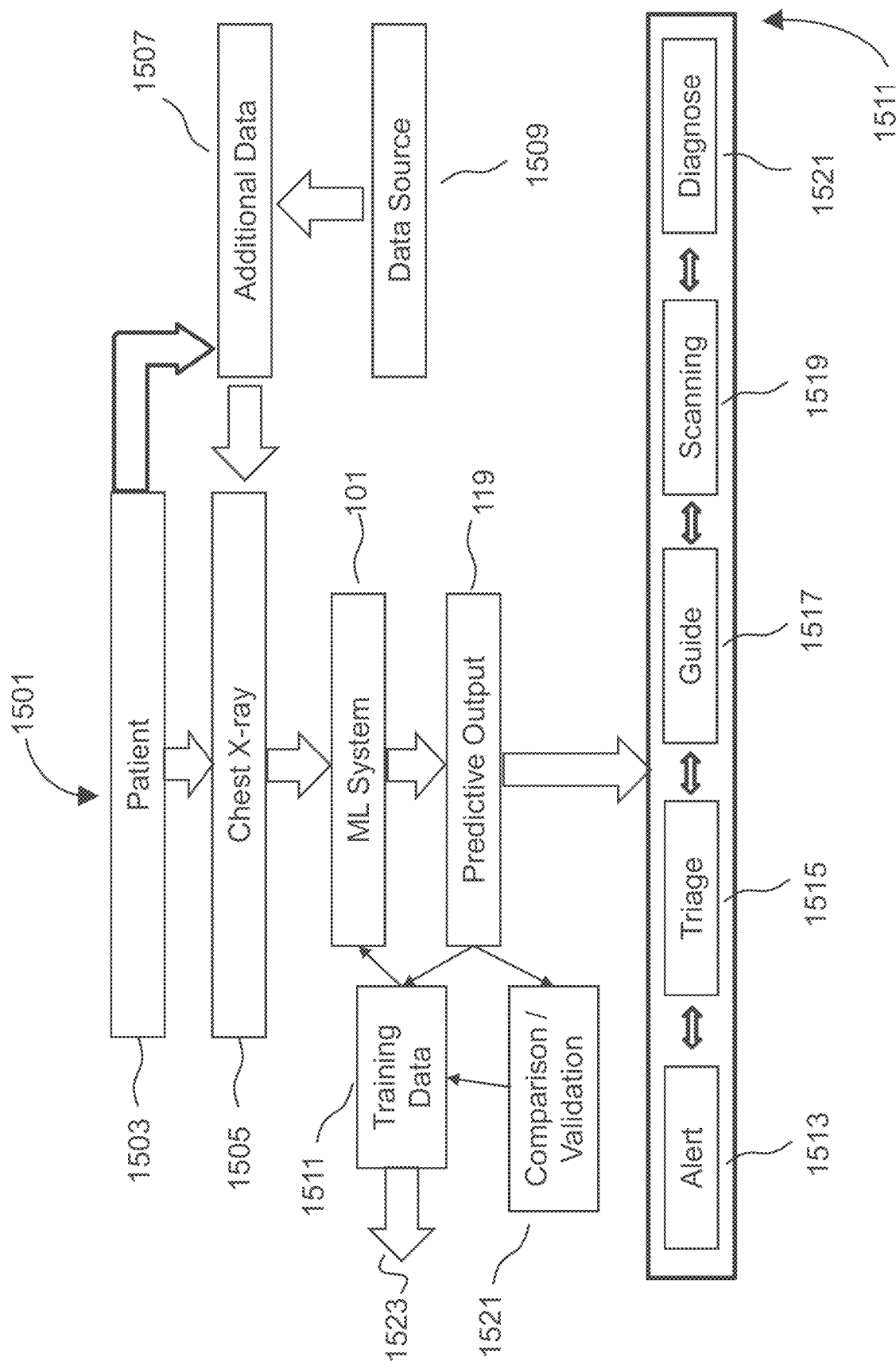
FIG. 15 shows a method using the ML systems of the invention.

FIG. 15 provides an exemplary method 1501 using an ML system 101 of the invention. In the method, a patient may arrive at a medical, research, or testing facility at which they receive a chest x-ray 1505. The chest x-ray 1505 may be annotated with additional data 1507. This additional data may include, for example, prior chest x-rays and CT scans, bioassay data (e.g., sputum cytology or genomic data), the patient's age, sex, ethnicity, comorbidities, clinical outcomes, medical treatments and history, and familial history. This data 1507 may come directly from the patient 1505, e.g. through interview, exam, or direct measurement. The data 1507 may also come from a data source 1509 such as an EMR system or a PACS.

In certain aspects, the patient may receive a chest x-ray as part of a lung cancer screening or another routine or follow-up screening. In these instances the data 1507 may include prior chest x-rays, which can be used for longitudinal screening. In certain aspects, the patient 1505 may arrive at a medical facility and present symptoms indicative of a lung abnormality, e.g., coughing, chest pain, breathing difficulties, and/or hemoptysis. The additional data 1507 may include these symptoms.

As shown in FIG. 15 the ML system 101 analyzes the chest x-ray 1505 and provides a predictive output 119. The ML system 101 may undertake one or more actions 1511 if it obtains a predictive output indicative of a lung abnormality, such as a lung nodule, or a lung pathology, such as cancer.

For example, the ML system may provide an alert regarding the patient's chest x-ray analysis. The alert may be sent, for example, to a radiologist or other specialist. In certain aspects, the alert may be sent to a medical professional treating the patient, such as a physician or nurse. This can be critical in emergency department and outpatient clinical settings. The alert can quickly inform a medical professional of the analysis before the patient leaves. The ML system 101, thus provides a window of time during which the patient can be informed about the analysis and undergo follow-up examination and screening. This is important because patients may be difficult to contact or reluctant to return for additional examination and/or screening once they leave a facility.

In certain aspects, the action 1511 may include the system triaging 1515 the chest x-ray for human review. For example, the system may flag the chest x-ray or move it ahead in a queue of x-rays to be reviewed by a radiologist or other specialist. In certain aspects, triaging may include sending the x-ray to an external specialist for review if such a specialist is unavailable at the facility to review the x-ray. The system 101 may also guide or assist 1515 a radiologist or other specialist in analyzing the chest x-ray image. This may include, for example, providing bounded potential lung abnormalities on the chest x-ray image. The system 101 can also suggest that the patient 1505 undergo additional screening 1519. The system 101 may also provide a diagnosis 1521 of a lung abnormality and/or pathology.

In certain aspects, the predictive output can be used as training data 1511 to train the ML system 101. The training data 1511 may contain a comparison or validation 1521 of the predictive output with an analysis of the x-ray image completed by a human-in-loop or another machine learning system. In certain aspects, the comparison or validation 1521 includes a human-in-loop reviewing the chest x-ray without being guided by the predictive output. Alternatively or additionally, the human-in-loop may review the chest x-ray guided by annotations on the chest x-ray provided by the predictive output.

Figure 16A:
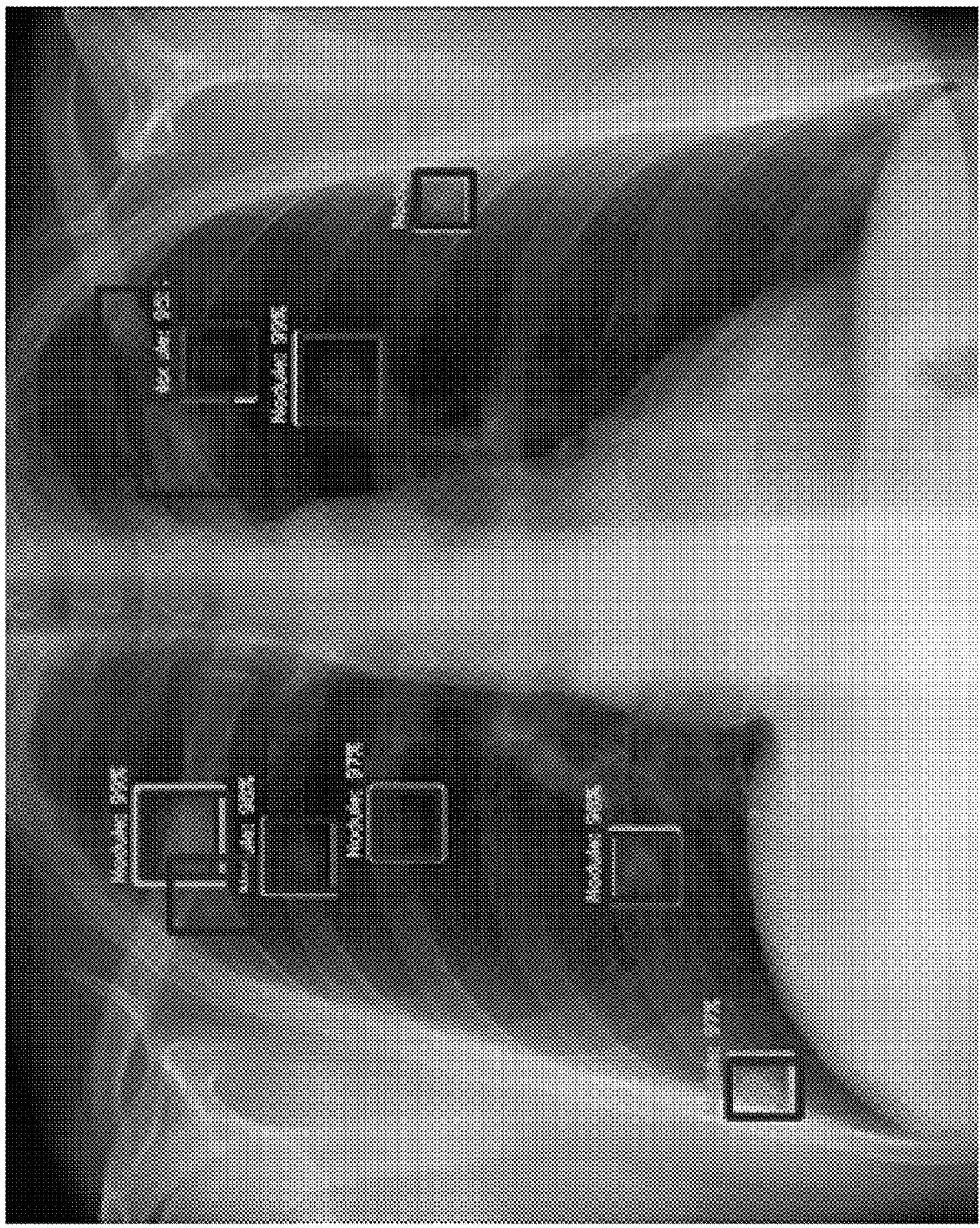
FIGS. 16A-16B show validations and comparisons of chest x-rays analyzed by an ML system and a radiologist.
Figure 16B:
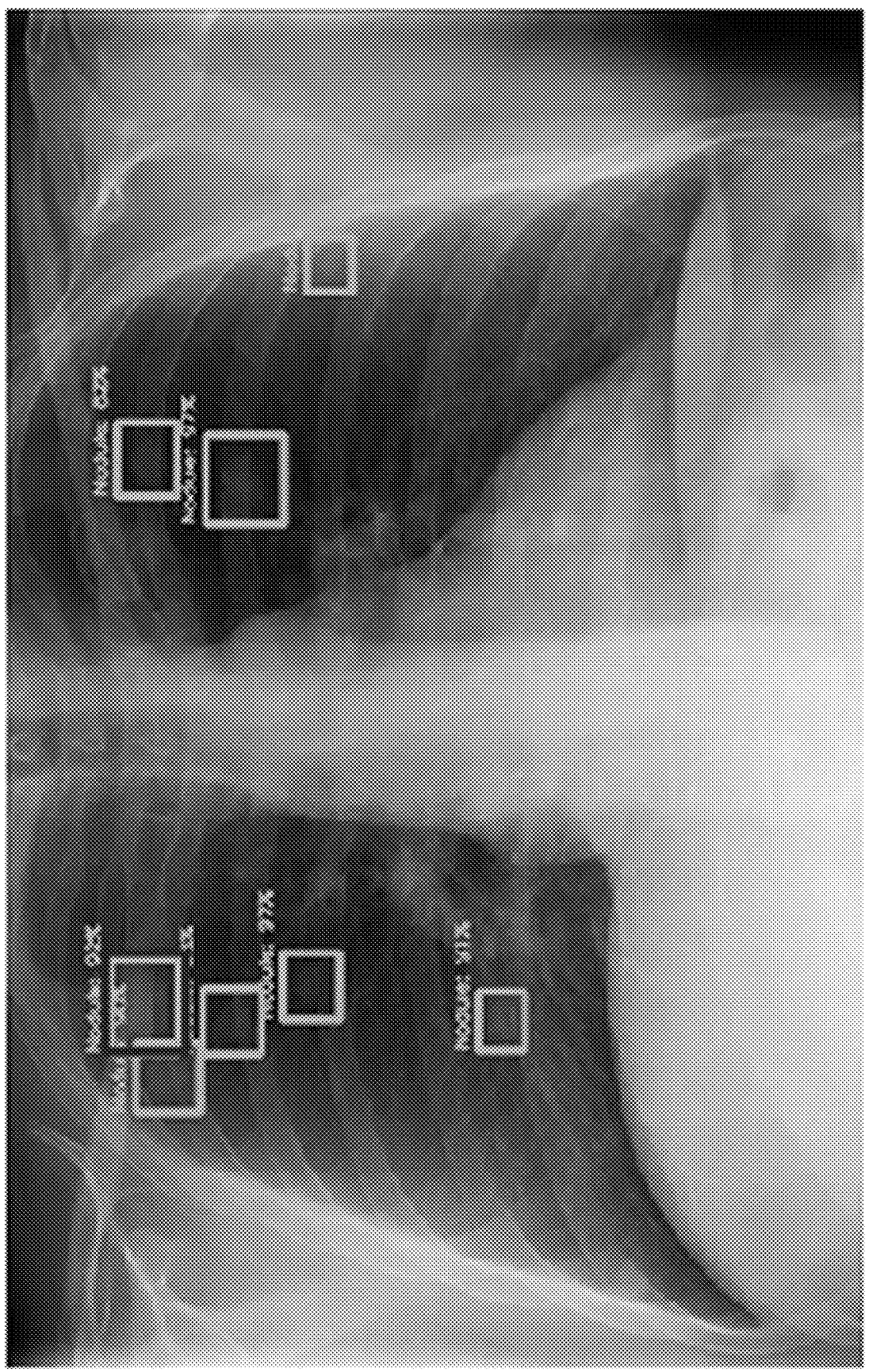

As shown in FIGS. 16A-16B, the ML systems of the invention can be continually trained to provide more detailed and accurate results. FIG. 16A shows a chest x-ray image with annotations from a predictive output shown in green and annotations from a radiologist made in red. The predictive output annotations are the locations and confidence values of lung nodules identified by the ML system. The radiologist annotations are locations of lung nodules identified by the radiologist. As can be seen, all lung nodules identified by the by the ML system were validated by the radiologist. However, the radiologist identified nodules not detected by the ML system. This comparison data can be used to train the ML system and improve its accuracy.

As shown in FIG. 16B, the accuracy of the ML system can be improved through additional training such that it detects far more lung nodules (green annotations) with a high confidence interval compared to a radiologist (red annotations). Thus, the ML systems of the invention can be trained to surpass the diagnostic abilities of a human.

The present invention includes systems and methods that use machine learning (ML) to detect lung abnormalities in chest x-rays, and also the train the ML systems of the invention to increase their accuracy and predictive value.

Machine learning is branch of computer science in which machine-based approaches are used to make predictions. (Bera et al., Nat Rev Clin Oncol., 16(11):703-715 (2019)). ML-based approaches involve a system learning from data fed into it, and use this data to make and/or refine predictions. As a generalization, a ML model learns from examples fed into it. Id. Over time, the ML model learns from these examples and creates new models and routines based on acquired information. Id. As a result, an ML model may create new correlations, relationships, routines or processes never contemplated by a human. A subset of ML is deep learning (DL). (Bera et al. (2019)). DL uses artificial neural networks. A DL network generally comprises layers of artificial neural networks. Id. These layers may include an input layer, an output layer, and multiple hidden layers. Id. DL has been shown to learn and form relationships that exceed the capabilities of humans.

By combining the ability of ML, including DL, to develop novel routines, correlations, relationships and processes amongst vast data sets including chest x-rays, CT scans, and patients' pathologies, clinical outcomes and diagnoses, the methods and systems of the disclosure can provide accurate diagnoses, prognoses, and treatment suggestions tailored to specific patients and patient groups afflicted with diseases, including lung cancer.

Using the objective nature of ML, analyzing diseases can be improved using the systems and methods of the disclosure. This includes using ML predictions as a companion to the decision making of trained specialists, or using ML to create independent predictions. Advantageously, ML models can be trained in such a way that they do not have preconceived notions of human specialists, and thus correlate certain image features without the inherent bias of a human.

ML systems of the invention can be trained with data sets that contain, for example, x-ray images, CT scan images and known patient outcomes, to identify features within the images in an unsupervised manner and to create a map of outcome probabilities over the features. The ML models can receive images from patients, identify within the images predictive features learned from the training steps and locate the predictive features on the map of outcome probabilities to provide a prognosis or diagnosis.

This finds particular use in longitudinal monitoring of patients/tumors. This process can be iterated over time to determine, for example, a subject's response to treatment, to assess the heterogeneous nature of a lung nodule, and/or to find one or more subtypes of cancer associated with a tumor.

ML systems of the disclosure can analyze images, such as a chest x-ray, and detect features based on, for example, pixel intensity and whether the pixel intensity meets a certain threshold. During ML training, these results can be confirmed and compared to those of human specialists viewing the same images.

The systems and methods of the disclosure can include providing an ML system with an x-ray or other image data (such as a CT scan) and operating the machine learning system to detect and annotate features within the image data. The image data can represent a portion, or a subset, of a total image. The ML system can be used to detect and annotate features, such as, for example, lung abnormalities, including lung nodules.

Figure 17:
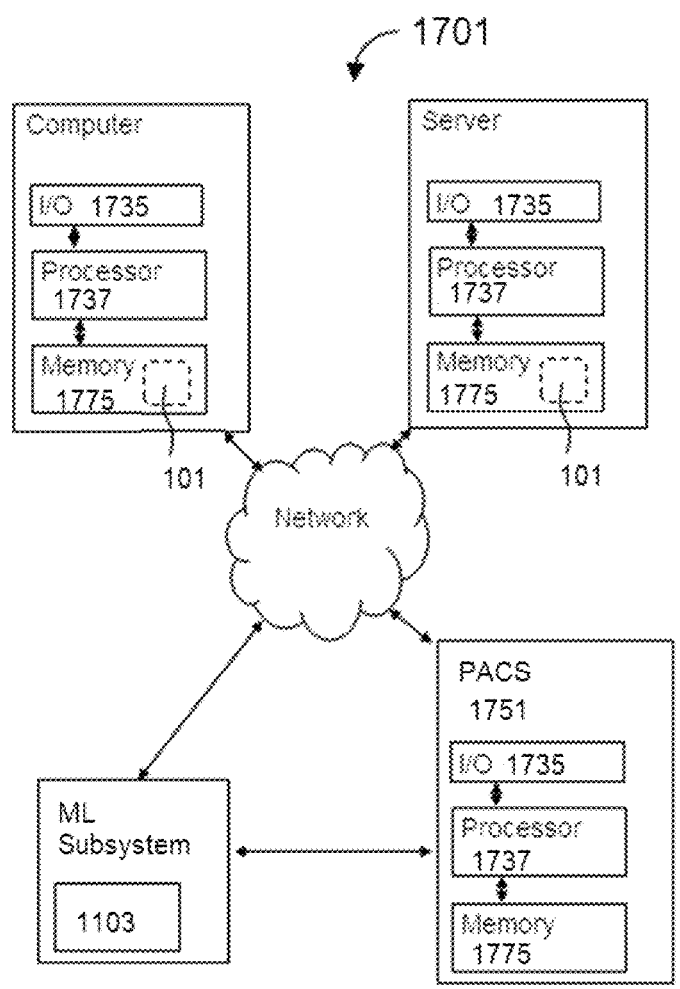
FIG. 17 shows an exemplary system of the invention.

FIG. 17 shows a computer system 1701 that may include an ML system 101 of the invention. The system 1701 includes at least one processor 1737 coupled to a memory subsystem 1775 including instructions executable by the processor 1737 to cause the system analyze a chest x-ray and to provide a predictive output 119.

The system 1701 includes at least one computer 2173. Optionally, the system 1701 may further include one or more of a server computer 1709, which can include the ML system 101, and/or one or more ML subsystems 1103 which may be distributed at various locations. Each computer in the system 1701 includes a processor 1737 coupled to a tangible, non-transitory memory 1775 device and at least one input/output device 1735. The system 1701 includes at least one processor 1737 coupled to a memory subsystem 1775.

The system 1701 may include one or more PACS 1751 for storing and manipulating chest x-rays and CT scans, including the standardized CT scans. The PACS 1751 may also store training data in accordance with the present disclosure. The PACS 1751 may be located at a hospital or other research institution.

The components (e.g., computer, server, PACS, and assay instruments) may be in communication over a network 1715 that may be wired or wireless and wherein the components may be remotely located. Using those mechanical components, the system 1701 is operable to receive or obtain training data such (e.g., chest x-rays, CT scans, and know pathology results) and chest x-rays for analysis. The system may use the memory to store the received data as well as the machine learning system data which may be trained and otherwise operated by the processor.

Processor refers to any device or system of devices that performs processing operations. A processor will generally include a chip, such as a single core or multi-core chip (e.g., 12 cores), to provide a central processing unit (CPU). In certain embodiments, a processor may be a graphics processing unit (GPU) such as an NVidia Tesla K80 graphics card from NVIDIA Corporation (Santa Clara, CA). A processor may be provided by a chip from Intel or AMD. A processor may be any suitable processor such as the microprocessor sold under the trademark XEON E5-2620 v3 by Intel (Santa Clara, CA) or the microprocessor sold under the trademark OPTERON 6200 by AMD (Sunnyvale, CA). Computer systems of the invention may include multiple processors including CPUs and or GPUs that may perform different steps of methods of the invention.

The memory subsystem 1775 may contain one or any combination of memory devices. A memory device is a mechanical device that stores data or instructions in a machine-readable format. Memory may include one or more sets of instructions (e.g., software) which, when executed by one or more of the processors of the disclosed computers can accomplish some or all of the methods or functions described herein. Preferably, each computer includes a non-transitory memory device such as a solid state drive, flash drive, disk drive, hard drive, subscriber identity module (SIM) card, secure digital card (SD card), micro SD card, or solid-state drive (SSD), optical and magnetic media, others, or a combination thereof.

Using the described components, the system 2171 is operable to produce a report and provide the report to a user via an input/output device. The output may include the predictive output 119. An input/output device is a mechanism or system for transferring data into or out of a computer. Exemplary input/output devices include a video display unit (e.g., a liquid crystal display (LCD) or a cathode ray tube (CRT)), a printer, an alphanumeric input device (e.g., a keyboard), a cursor control device (e.g., a mouse), a disk drive unit, a speaker, a touchscreen, an accelerometer, a microphone, a cellular radio frequency antenna, and a network interface device, which can be, for example, a network interface card (NIC), Wi-Fi card, or cellular modem.

Any of several suitable types of machine learning may be used for one or more steps of the disclosed methods. Suitable machine learning types may include neural networks, decision tree learning such as random forests, support vector machines (SVMs), association rule learning, inductive logic programming, regression analysis, clustering, Bayesian networks, reinforcement learning, metric learning, and genetic algorithms. One or more of the machine learning approaches (aka type or model) may be used to complete any or all of the method steps described herein.

For example, one model, such as a neural network, may be used to complete the training steps of autonomously identifying features in chest x-rays and/or CT scans and associating those features with certain outcomes. Once those features are learned, they may be applied to test samples by the same or different models or classifiers (e.g., a random forest, SVM, regression) for the correlating steps. In certain embodiments, features may be identified using one or more machine learning systems and the associations may then be refined using a different machine learning system. Accordingly some of the training steps may be unsupervised using unlabeled data while subsequent training steps (e.g., association refinement) may use supervised training techniques such as regression analysis using the features autonomously identified by the first machine learning system.

In decision tree learning, a model is built that predicts that value of a target variable based on several input variables. Decision trees can generally be divided into two types. In classification trees, target variables take a finite set of values, or classes, whereas in regression trees, the target variable can take continuous values, such as real numbers. Examples of decision tree learning include classification trees, regression trees, boosted trees, bootstrap aggregated trees, random forests, and rotation forests. In decision trees, decisions are made sequentially at a series of nodes, which correspond to input variables. Random forests include multiple decision trees to improve the accuracy of predictions. See Breiman, 2001, Random Forests, Machine Learning 45:5-32, incorporated herein by reference. In random forests, bootstrap aggregating or bagging is used to average predictions by multiple trees that are given different sets of training data. In addition, a random subset of features is selected at each split in the learning process, which reduces spurious correlations that can results from the presence of individual features that are strong predictors for the response variable. Random forests can also be used to determine dissimilarity measurements between unlabeled data by constructing a random forest predictor that distinguishes the observed data from synthetic data. Id.; Shi, T., Horvath, S. (2006), Unsupervised Learning with Random Forest Predictors, Journal of Computational and Graphical Statistics, 15(1):118-138, incorporated herein by reference. Random forests can accordingly by used for unsupervised machine learning methods of the invention.

SVMs are useful for both classification and regression. When used for classification of new data into one of two categories, such as having a disease or not having the disease, an SVM creates a hyperplane in multidimensional space that separates data points into one category or the other. Although the original problem may be expressed in terms that require only finite dimensional space, linear separation of data between categories may not be possible in finite dimensional space. Consequently, multidimensional space is selected to allow construction of hyperplanes that afford clean separation of data points. See Press, W. H. et al., Section 16.5. Support Vector Machines. Numerical Recipes: The Art of Scientific Computing (3rd ed.). New York: Cambridge University (2007), incorporated herein by reference. SVMs can also be used in support vector clustering to perform unsupervised machine learning suitable for some of the methods discussed herein. See Ben-Hur, A., et al., (2001), Support Vector Clustering, Journal of Machine Learning Research, 2:125-137.

Regression analysis is a statistical process for estimating the relationships among variables such as features and outcomes. It includes techniques for modeling and analyzing relationships between multiple variables. Specifically, regression analysis focuses on changes in a dependent variable in response to changes in single independent variables. Regression analysis can be used to estimate the conditional expectation of the dependent variable given the independent variables. The variation of the dependent variable may be characterized around a regression function and described by a probability distribution. Parameters of the regression model may be estimated using, for example, least squares methods, Bayesian methods, percentage regression, least absolute deviations, nonparametric regression, or distance metric learning.

Association rule learning is a method for discovering interesting relations between variables in large databases. See Agrawal, 1993, Mining association rules between sets of items in large databases, Proc 1993 ACM SIGMOD Int Conf Man Data p. 207, incorporated by reference. Algorithms for performing association rule learning include Apriori, Eclat, FP-growth, and AprioriDP. FIN, PrePost, and PPV, which are described in detail in Agrawal, 1994, Fast algorithms for mining association rules in large databases, in Bocca et al., Eds., Proceedings of the 20th International Conference on Very Large Data Bases (VLDB), Santiago, Chile, September 1994, pages 487-499; Zaki, 2000, Scalable algorithms for association mining, IEEE Trans Knowl Data Eng 12(3):372-390; Han, 2000, Mining Frequent Patterns Without Candidate Generation, Proc 2000 ACM SIGMOD Int Conf Management of Data; Bhalodiya, 2013, An Efficient way to find frequent pattern with dynamic programming approach, NIRMA Univ Intl Conf Eng, 28-30 Nov. 2013; Deng, 2014, Fast mining frequent itemsets using Nodesets, Exp Sys Appl 41(10):4505-4512; Deng, 2012, A New Algorithm for Fast Mining Frequent Itemsets Using N-Lists, Science China Inf Sci 55(9): 2008-2030; and Deng, 2010, A New Fast Vertical Method for Mining Frequent Patterns, Int J Comp Intel Sys 3(6):333-344, the contents of each of which are incorporated by reference. Inductive logic programming relies on logic programming to develop a hypothesis based on positive examples, negative examples, and background knowledge. See Luc De Raedt. A Perspective on Inductive Logic Programming. The Workshop on Current and Future Trends in Logic Programming, Shakertown, to appear in Springer LNCS, 1999; Muggleton, 1993, Inductive logic programming: theory and methods, J Logic Prog 19-20:629-679, incorporated herein by reference.

Bayesian networks are probabilistic graphical models that represent a set of random variables and their conditional dependencies via directed acyclic graphs (DAGs). The DAGs have nodes that represent random variables that may be observable quantities, latent variables, unknown parameters or hypotheses. Edges represent conditional dependencies; nodes that are not connected represent variables that are conditionally independent of each other. Each node is associated with a probability function that takes, as input, a particular set of values for the node's parent variables, and gives (as output) the probability (or probability distribution, if applicable) of the variable represented by the node. See Charniak, 1991, Bayesian Networks without Tears, AI Magazine, p. 50, incorporated by reference.

The machine learning system 101 includes at least two neural networks. The machine learning system 101 may include neural networks that are deep-learning neural networks, which include an input layer, an output layer, and a plurality of hidden layers.

A neural network, which is modeled on the human brain, allows for processing of information and machine learning. A neural network may includes nodes that mimic the function of individual neurons, and the nodes are organized into layers. The neural network includes an input layer, an output layer, and one or more hidden layers that define connections from the input layer to the output layer. The neural network may, for example, have multiple nodes in the output layer and may have any number of hidden layers. The total number of layers in a neural network depends on the number of hidden layers. For example, the neural network may include at least 5 layers, at least 10 layers, at least 15 layers, at least 20 layers, at least 25 layers, at least 30 layers, at least 40 layers, at least 50 layers, or at least 100 layers. The nodes of the neural network serve as points of connectivity between adjacent layers. Nodes in adjacent layers form connections with each other, but nodes within the same layer do not form connections with each other. The neural network has an input layer, n hidden layers, and an output layer. Each layer may comprise a number of nodes.

The system may include any neural network that facilitates machine learning. The system may include a known neural network architecture, such as GoogLeNet (Szegedy, et al. Going deeper with convolutions, in CVPR 2015, 2015); AlexNet (Krizhevsky, et al. Imagenet classification with deep convolutional neural networks, in Pereira, et al. Eds., Advances in Neural Information Processing Systems 25, pages 1097-3105, Curran Associates, Inc., 2012); VGG16 (Simonyan & Zisserman, Very deep convolutional networks for large-scale image recognition, CoRR, abs/3409.1556, 2014); or FaceNet (Wang et al., Face Search at Scale: 90 Million Gallery, 2015), each of the aforementioned references are incorporated by reference.

Training data may include chest x-rays, CT scans, additional clinical data, such as patient outcomes, known pathology results, and/or any data relevant to the chest x-ray that the neural network will analyze, which itself may be annotated. Nodes in the input layer receive a chest x-ray, which may be annotated.

Deep learning (also known as deep structured learning, hierarchical learning or deep machine learning) is a class of machine learning operations that use a cascade of many layers of nonlinear processing units for feature extraction and transformation. Each successive layer uses the output from the previous layer as input. The algorithms may be supervised or unsupervised and applications include pattern analysis (unsupervised) and classification (supervised). Certain embodiments are based on unsupervised learning of multiple levels of features or representations of the data. Higher level features are derived from lower level features to form a hierarchical representation. Those features are preferably represented within nodes as feature vectors.

Deep learning by the neural network includes learning multiple levels of representations that correspond to different levels of abstraction; the levels form a hierarchy of concepts. In most preferred embodiments, the neural network includes at least 5 and preferably more than 10 hidden layers. The many layers between the input and the output allow the system to operate via multiple processing layers.

Deep learning is part of a broader family of machine learning methods based on learning representations of data. An observation (e.g., an image) can be represented in many ways such as a vector of intensity values per pixel, or in a more abstract way as a set of edges, regions of particular shape, etc. Those features are represented at nodes in the network. Preferably, each feature is structured as a feature vector, a multi-dimensional vector of numerical features that represent some object. The feature provides a numerical representation of objects, since such representations facilitate processing and statistical analysis. Feature vectors are similar to the vectors of explanatory variables used in statistical procedures such as linear regression. Feature vectors are often combined with weights using a dot product in order to construct a linear predictor function that is used to determine a score for making a prediction.

The vector space associated with those vectors may be referred to as the feature space. In order to reduce the dimensionality of the feature space, dimensionality reduction may be employed. Higher-level features can be obtained from already available features and added to the feature vector, in a process referred to as feature construction. Feature construction is the application of a set of constructive operators to a set of existing features resulting in construction of new features.

Within the network, nodes are connected in layers, and signals travel from the input layer to the output layer. In certain embodiments, each node in the input layer corresponds to a respective one of the patches from the training data. The nodes of the hidden layer are calculated as a function of a bias term and a weighted sum of the nodes of the input layer, where a weight is assigned to each connection between a node of the input layer and a node in the hidden layer. The bias term and the weights between the input layer and the hidden layer are learned autonomously in the training of the neural network. The network may include thousands or millions of nodes and connections. Typically, the signals and state of artificial neurons are real numbers, typically between 0 and 1. Optionally, there may be a threshold function or limiting function on each connection and on the unit itself, such that the signal must surpass the limit before propagating. Back propagation is the use of forward stimulation to modify connection weights, and is sometimes done to train the network using known correct outputs.

Systems and methods of the disclosure may use convolutional neural networks (CNN). A CNN is a feedforward network comprising multiple layers to infer an output from an input. CNNs are used to aggregate local information to provide a global predication. CNNs use multiple convolutional sheets from which the network learns and extracts feature maps using filters between the input and output layers. The layers in a CNN connect at only specific locations with a previous layer. Not all neurons in a CNN connect. CNNs may comprise pooling layers that scale down or reduce the dimensionality of features. CNNs hierarcially deconstruct data into general, low-level cues, which are aggregated to form higher-order relationships to identify features of interest. CNNs predictive utility is in learning repetitive features that occur throughout a data set.

The systems and methods of the disclosure may use fully convolutional networks (FCN). In contrast to CNNs, FCNs can learn representations locally within a data set, and therefore, can detect features that may occur sparsely within a data set.

The systems and methods of the disclosure may use recurrent neural networks (RNN). RNNs have an advantage over CNNs and FCNs in that they can store and learn from inputs over multiple time periods and process the inputs sequentially.

The systems and methods of the disclosure may use generative adversarial networks (GAN), which find particular application in training neural networks. One network is fed training exemplars from which it produces synthetic data. The second network evaluates the agreement between the synthetic data and the original data. This allows GANs to improve the prediction model of the second network.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

REFERENCES

Information may be found in:
(1) American Cancer Society, Lung Cancer, Cancer A-Z www.cancer.org/cancer/lung-cancer.html, Accessed Oct. 16, 2020;
(2) World Health Organization, Cancer Key Facts, 2018; www.who.int/news-room/fact-sheets/detail/cancer, Accessed Oct. 16, 2020;
(3) SEER Cancer Statistics Review, 1975-2017, Bethesda, MD, seer.cancer.gov/csr/1975_2017/, based on November 2019 SEER data submission, posted to the SEER web site: National Cancer Institute; April 2020;
(4) National Cancer Institute, Cancer Stat Facts: Lung and Bronchus Cancer, seer.cancer.gov/statfacts/html/lungb.html, Accessed Oct. 16, 2020;
(5) Cronin K A, Lake A J, Scott S, et al, Annual Report to the Nation on the Status of Cancer, part I: National cancer statistics, Cancer, 2018, 124(13):2785-2800;
(6) Del Ciello A, Franchi P, Contegiacomo A, Cicchetti G, Bonomo L, Larici A R, Missed lung cancer: when, where, and why? Diagn Interv Radiol, 2017, 23(2):118-126;
(7) National Lung Screening Trial Research T, Aberle D R, Adams A M, et al, Reduced lung-cancer mortality with low-dose computed tomographic screening, The New England journal of medicine, 2011, 365(5):395-409;
(8) Duan S, Cao H, Liu H, et al, Development of a machine learning-based multimode diagnosis system for lung cancer, Aging (Albany NY), 2020, 12(10):9840-9854;
(9) Myers L C, Skillings J, Heard L, Metlay J P, Mort E, Medical Malpractice Involving Pulmonary/Critical Care Physicians, Chest, 2019, 156(5):907-914;
(10) Baker S R, Patel R H, Yang L, Lelkes V M, Castro A, 3rd, Malpractice suits in chest radiology: an evaluation of the histories of 8265 radiologists, Journal of thoracic imaging, 2013, 28(6):388-391;
(11) Aaronson E L, Quinn G R, Wong C I, et al, Missed diagnosis of cancer in primary care: Insights from malpractice claims data, J Healthc Risk Manag, 2019; 39(2):19-29;
(12) Gould M K, Donington J, Lynch W R, et al, Evaluation of individuals with pulmonary nodules: when is it lung cancer? Diagnosis and management of lung cancer, 3rd ed: American College of Chest Physicians evidence-based clinical practice guidelines, Chest, 2013; 143(5 Suppl):e93S-e120S;
(13) MacMahon H, Naidich D P, Goo J M, et al, Guidelines for Management of Incidental Pulmonary Nodules Detected on CT Images: From the Fleischner Society 2017, Radiology, 2017, 284(1):228-243;
(14) Leung C, Shaipanich T, Current Practice in the Management of Pulmonary Nodules Detected on Computed Tomography Chest Scans, Can Respir J, 2019, 2019:9719067-9719067;
(15) Blagev D P, Lloyd J F, Conner K, et al, Follow-up of Incidental Pulmonary Nodules and the Radiology Report, Journal of the American College of Radiology: JACR, 2016, 13(2 Suppl):R18-24;
(16) Kakeda S, Moriya J, Sato H, et al, Improved detection of lung nodules on chest radiographs using a commercial computer-aided diagnosis system, AJR Am J Roentgenol, 2004, 182(2):505-510;
(17) White C S, Flukinger T, Jeudy J, Chen J J, Use of a computer-aided detection system to detect missed lung cancer at chest radiography, Radiology, 2009, 252(1):273-281;
(18) Gao Y, Geras K J, Lewin A A, Moy L, New Frontiers: An Update on Computer-Aided Diagnosis for Breast Imaging in the Age of Artificial Intelligence, AJR American journal of roentgenology, 2019, 212(2):300-307;
(19) Cios K J, William Moore G, Uniqueness of medical data mining, Artificial Intelligence in Medicine, 2002, 26(1):1-24;
(20) Choy G, Khalilzadeh O, Michalski M, et al, Current Applications and Future Impact of Machine Learning in Radiology, Radiology, 2018, 288(2):318-328;
(21) Ritchie A J, Sanghera C, Jacobs C, et al, Computer Vision Tool and Technician as First Reader of Lung Cancer Screening CT Scans, J Thorac Oncol, 2016, 11(5):709-717;
(22) Liu B, Chi W, Li X, et al, Evolving the pulmonary nodules diagnosis from classical approaches to deep learning-aided decision support: three decades' development course and future prospect, Journal of cancer research and clinical oncology, 2020, 146(1):153-185;
(23) Rubin G D, Lung nodule and cancer detection in computed tomography screening, Journal of thoracic imaging, 2015, 30(2):130-138;
(24) Harrell F E, Regression modeling strategies: with applications to linear models, logistic regression, and survival analysis, New York: Springer, 2001;
(25) Hajian-Tilaki K, Receiver Operating Characteristic (ROC) Curve Analysis for Medical Diagnostic Test Evaluation, Caspian J Intern Med, 2013, 4(2):627-635;
(26) AAMI TIR45: 2012/(R)2018 Guidance on the use of AGILE practices in the development of medical device software, Arlington, VA: Association for the Advancement of Medical Instrumentation, 2018;
(27) Applying Human Factors and Usability Engineering to Medical Devices, Rockville, MD: Food and Drug Administration, 2016;
(28) Shinagare A B, Boland G W, Di Carli M, et al, Diagnostic Certainty Scale, Brigham Health/Dana-Farber Department of Radiology, 2020, rad.bwh.harvard.edu/diagnostic-certainty-scale, Accessed May 29 2020; and
(29) Jang S, Song H, Shin Y J, et al, Deep Learning-based Automatic Detection Algorithm for Reducing Overlooked Lung Cancers on Chest Radiographs, Radiology, 2020, 296(3):652-661, the full contents of each of those 29 references are incorporated by reference.

The invention claimed is:

1. A diagnostic method, the method comprising: providing an image file of a chest x-ray from a patient to a machine learning system that has been trained on training data only available at a plurality of sources separated by time and/or geography and the training comprises connecting the machine learning system to the plurality of sources at different times and/or locations, wherein the machine learning system operates by resizing the image file of the chest x-ray into a first image that depicts the entire x-ray at a reduced resolution and placing a subsection of the file into a second image at an original resolution; analyzing the first and second images in parallel by respective first and second neural networks to output scores indicating a probability of a nodule, wherein the machine learning system has been trained to learn associations between features in chest x-rays and known pathology results with an area under the curve (AUC) of true positives over false positives for learned feature associations is between 0.7 and 0.83; and operating the machine learning system to detect lung nodules.

2. The method of claim 1, wherein connecting the machine learning system to the plurality of sources provides a federated learning model by which patient data does not leave any of the plurality of sources.

3. The method of claim 2, wherein the machine learning system comprises a plurality of distributed machine learning (ML) subsystems using a federated learning model to provide the machine learning system trained to detect abnormalities in chest x-rays.

4. The method of claim 1, wherein the machine learning system is further trained on CT scans from the subjects to affirm or negate learned feature associations.

5. The method of claim 4, wherein the CT scans are obtained as diverse CT scans from different instruments operating under diverse imaging conditions or parameters, the method further comprising reconstructing a standardized CT scan from each of the diverse CT scans.

6. The method of claim 5, wherein the system includes a GAN trained to reconstruct standardized CT scans from the diverse CT scans and to augment the training data to make the neural networks generalizable across a plurality of image acquisition equipment and parameters.

7. The method of claim 1, wherein the AUC≥0.74 is achieved by unsupervised learning without the aid of human once the learning is initiated.

8. The method of claim 1, further comprising a human-in-loop training step that includes: displaying the chest x-ray to a clinician;
receiving at the machine learning system an annotation from the clinician that identifies a lung nodule in the chest x-ray;
comparing by the machine learning system the annotation to one of the scores indicating a probability of a nodule; and
using the comparison to improve learned feature associations.

9. The method of claim 1, further comprising the machine learning system providing an alert that the system detected an abnormality in the chest x-ray from the subject and/or providing a region proposal including the abnormality in the chest x-ray.

10. The method of claim 9, further comprising triaging the chest x-ray for immediate review by a human.

11. The method of claim 1, further comprising characterizing an identified lung nodule with the machine learning system.

12. The method of claim 11, wherein characterizing includes: classifying a nodule as a tumor, benign and/or malignant, and/or assessing or predicting nodule progression, volumetric sizing, nodule etiology, nodule histology, and/or response to treatment.

* * * * *